(12) United States Patent
Faraday

(10) Patent No.: US 9,585,899 B2
(45) Date of Patent: Mar. 7, 2017

(54) METHOD OF INHIBITING PLATELET AGGREGATION AND CLOT FORMATION

(75) Inventor: Nauder Faraday, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 940 days.

(21) Appl. No.: 12/665,859

(22) PCT Filed: Jun. 19, 2008

(86) PCT No.: PCT/US2008/007643
§ 371 (c)(1),
(2), (4) Date: Jan. 13, 2011

(87) PCT Pub. No.: WO2008/156807
PCT Pub. Date: Dec. 24, 2008

(65) Prior Publication Data
US 2011/0104146 A1   May 5, 2011

Related U.S. Application Data

(60) Provisional application No. 60/936,229, filed on Jun. 19, 2007.

(51) Int. Cl.
| | | |
|---|---|---|
| *A61K 38/06* | (2006.01) | |
| *A61K 38/07* | (2006.01) | |
| *A61K 38/55* | (2006.01) | |
| *A61K 31/616* | (2006.01) | |
| *A61K 38/17* | (2006.01) | |

(52) U.S. Cl.
CPC ............ *A61K 31/616* (2013.01); *A61K 38/06* (2013.01); *A61K 38/07* (2013.01); *A61K 38/1709* (2013.01); *A61K 38/55* (2013.01)

(58) Field of Classification Search
CPC ...... A61K 38/07; A61K 38/55; A61K 31/616; A61K 2300/00
See application file for complete search history.

(56) References Cited

U.S. PATENT DOCUMENTS

| | | |
|---|---|---|
| 2001/0056180 A1 | 12/2001 | Thompson et al. |
| 2004/0052791 A1 | 3/2004 | Ehrhardt et al. |
| 2005/0095246 A1 | 5/2005 | Shafer |
| 2005/0255484 A1 | 11/2005 | Valkirs et al. |
| 2006/0046961 A1 | 3/2006 | McKay et al. |
| 2006/0210536 A1 | 9/2006 | Horvath et al. |
| 2007/0077201 A1 | 4/2007 | Reading et al. |

FOREIGN PATENT DOCUMENTS

WO   WO01/60401   *  8/2001

OTHER PUBLICATIONS

Greco, M.N. et al. Nonpeptide inhibitors of cathepsin G: Optimization of a novel beta-ketophosphonic acid lead by structure-based drug design. J. Am. Chem. Soc., 2002, vol. 124, p. 3810-3811.*
Santa Cruz Biotechnology, Inc. catalog, Cathepsin G Inhibitor I CAS (429676-93-7) sc-221399, Jun. 11, 2012.*
Sienczyk, M., et al. New potent cathepsin G phosphonate inhibitors. Bioorganic and Medicinal Chemistry, 2008, vol. 16, p. 8863-8867.*
Zani, M-L, et al. SLPS and trappin-2 as therapeutic agents to target airway serine proteases in inflammatory lung diseases: current and future directions. Biochem. Soc. Trans., 2011, vol. 39, p. 1441-1446.*
Lomas D.A., et al. The control of neutrophil chemotaxis by inhibitors of cathepsin G and chymotrypsin. J. Biol. Chem., 1995, vol. 270(40), p. 23437-23443.*
George-Gay, B. et al. Understanding the complete blood count with differential. J. PeriAnesthesia Nursing, 2003, vol. 18, No. 2, p. 96-117.*
Divani, A.A. et al. Antiplatelet therapy: Aspirin resistance and all that jazz! Clinical and Applied Thrombosis/Hemostasis, 2013, vol. 19, No. 1, p. 5-18.*
Floyd, C.N. et al. Mechanisms of aspirin resistance. Pharmacology and Therapeutics, 2014, vol. 141, p. 69-78.*
Grinstein, J. et al. Aspirin resistance: Current status and role of tailored therapy. Clinical Cardiology, 2012, vol. 35, No. 11, p. 673-681.*

* cited by examiner

*Primary Examiner* — Robert Landsman
*Assistant Examiner* — Bruce D Hissong
(74) *Attorney, Agent, or Firm* — Mintz Levin Cohn Ferris Glovsky and Popeo, P.C.; Peter F. Corless; Christopher R. Cowles

(57) ABSTRACT

The instant invention provides methods and compositions for the treatment, prevention and diagnosis of for example, platelet aggregation or clot formation in a subject. The invention inhibits the activity of decreases the amount of neutrophils in the subject by inhibiting the activity or production of IL-6, interferon-gamma, STAT1, or cathepsin G. The invention addresses decreasing the amount of neutrophils in an attempt to treat subjects that have or are at risk of developing a vascular occlusive disease, an ischemia or reperfusion injury, an acute or chronic inflammatory state, autoimmune disease, myelodysplastic syndrome, tissue injury from surgery or accidental trauma, acute bacterial or viral infection, has undergone a microvascular surgical reconstructive procedure, is receiving granulocyte colony stimulating factor therapy, receiving stem cell therapy, or has sickle cell anemia.

11 Claims, 12 Drawing Sheets

Figure 17

A) SEQ ID NO:1

>gi|10834984|ref|NP_000591.1| interleukin 6 [Homo sapiens]
MNSFSTSAFGPVAFSLGLLLVLPAAFPAPVPPGEDSKDVAAPHRQPLTSSERIDKQIRYILDGISALRKE
TCNKSNMCESSKEALAENNLNLPKMAEKDGCFQSGFNEETCLVKIITGLLEFEVYLEYLQNRFESSEEQA
RAVQMSTKVLIQFLQKKAKNLDAITTPDPTTNASLLTKLQAQNQWLQDMTTHLILRSFKEFLQSSLRALR
QM

B) SEQ ID NO:2

>gi|155369258|ref|NM_000600.2| Homo sapiens interleukin 6 (interferon, beta 2) (IL6),
mRNA
CATTCTGCCCTCGAGCCCACCGGGAACGAAAGAGAAGCTCTATCTCCCCTCCAGGAGCCCAGCTATGAAC
TCCTTCTCCACAAGCGCCTTCGGTCCAGTTGCCTTCTCCCTGGGGCTGCTCCTGGTGTTGCCTGCTGCCT
TCCCTGCCCCAGTACCCCCAGGAGAAGATTCCAAAGATGTAGCCGCCCCACACAGACAGCCACTCACCTC
TTCAGAACGAATTGACAAACAAATTCGGTACATCCTCGACGGCATCTCAGCCCTGAGAAAGGAGACATGT
AACAAGAGTAACATGTGTGAAAGCAGCAAAGAGGCACTGGCAGAAAACAACCTGAACCTTCCAAAGATGG
CTGAAAAAGATGGATGCTTCCAATCTGGATTCAATGAGGAGACTTGCCTGGTGAAAATCATCACTGGTCT
TTTGGAGTTTGAGGTATACCTAGAGTACCTCCAGAACAGATTTGAGAGTAGTGAGGAACAAGCCAGAGCT
GTGCAGATGAGTACAAAAGTCCTGATCCAGTTCCTGCAGAAAAAGGCAAAGAATCTAGATGCAATAACCA
CCCCTGACCCAACCACAAATGCCAGCCTGCTGACGAAGCTGCAGGCACAGAACCAGTGGCTGCAGGACAT
GACAACTCATCTCATTCTGCGCAGCTTTAAGGAGTTCCTGCAGTCCAGCCTGAGGGCTCTTCGGCAAATG
TAGCATGGGCACCTCAGATTGTTGTTGTTAATGGGCATTCCTTCTTCTGGTCAGAAACCTGTCCACTGGG
CACAGAACTTATGTTGTTCTCTATGGAGAACTAAAAGTATGAGCGTTAGGACACTATTTTAATTATTTTT
AATTTATTAATATTTAAATATGTGAAGCTGAGTTAATTTATGTAAGTCATATTTATATTTTTAAGAAGTA
CCACTTGAAACATTTTATGTATTAGTTTTGAAATAATAATGGAAAGTGGCTATGCAGTTTGAATATCCTT
TGTTTCAGAGCCAGATCATTTCTTGGAAAGTGTAGGCTTACCTCAAATAAATGGCTAACTTATACATATT
TTTAAAGAAATATTTATATTGTATTTATATAATGTATAAATGGTTTTTATACCAATAAATGGCATTTTAA
AAAATTCAGCA

Figure 18

A) SEQ ID NO:3

>gi|56786138|ref|NP_000610.2| interferon, gamma [Homo sapiens]
MKYTSYILAFQLCIVLGSLGCYCQDPYVKEAENLKKYFNAGHSDVADNGTLFLGILKNWKEESDRKIMQS
QIVSFYFKLFKNFKDDQSIQKSVETIKEDMNVKFFNSNKKKRDDFEKLTNYSVTDLNVQRKAIHELIQVM
AELSPAAKTGKRKRSQMLFRGRRASQ

B) SEQ ID NO:4

```
>gi|NM_000619|Homo sapiens interferon, gamma (IFNG)|1240 bp
    1 cacattgttc tgatcatctg aagatcagct attagaagag aaagatcagt taagtccttt
   61 ggacctgatc agcttgatac aagaactact gatttcaact tctttggctt aattctctcg
  121 gaaacgatga atatacaag ttatatcttg gcttttcagc tctgcatcgt tttgggttct
  181 cttggctgtt actgccagga cccatatgta aagaagcag aaaaccttaa gaaatatttt
  241 aatgcaggtc attcagatgt agcggataat ggaactcttt tcttaggcat tttgaagaat
  301 tggaaagagg agagtgacag aaaaataatg cagagccaaa ttgtctcctt ttacttcaaa
  361 cttttaaaa actttaaaga tgaccagagc atccaaaaga gtgtggagac catcaaggaa
  421 gacatgaatg tcaagttttt caatagcaac aaaaagaaac gagatgactt cgaaaagctg
  481 actaattatt cggtaactga cttgaatgtc aacgcaaag caatacatga actcatccaa
  541 gtgatggctg aactgtcgcc agcagctaaa acagggaagc gaaaaggag tcagatgctg
  601 tttcgaggtc gaagagcatc ccagtaatgg ttgtcctgcc tgcaatattt gaattttaaa
  661 tctaaatcta tttattaata tttaacatta tttatatggg aatatatttt ttagactcat
  721 caatcaaata agtatttata atagcaactt ttgtgtaatg aaaatgaata tctattaata
  781 tatgtattat ttataattcc tatatcctgt gactgtctca cttaatcctt tgttttctga
  841 ctaattaggc aaggctatgt gattacaagg ctttatctca ggggccaact aggcagccaa
  901 cctaagcaag atcccatggg ttgtgtgttt atttcacttg atgatacaat gaacacttat
  961 aagtgaagtg atactatcca gttactgccg gtttgaaaat atgcctgcaa tctgagccag
 1021 tgctttaatg gcatgtcaga cagaacttga atgtgtcagg tgaccctgat gaaaacatag
 1081 catctcagga gatttcatgc ctggtgcttc caaatattgt tgacaactgt gactgtaccc
 1141 aaatggaaag taactcattt gttaaaatta tcaatatcta atatatatga ataaagtgta
 1201 agttcacaac aaaaaaaaaa aaaaaaaaaa aaaaaaaaaa
```

FIGURE 19

A) SEQ ID NO:5

>gi|4503149|ref|NP_001902.1| cathepsin G preproprotein [Homo sapiens]
MQPLLLLLAFLLPTGAEAGEIIGGRESRPHSRPYMAYLQIQSPAGQSRCGGFLVREDFVLTAAHCWGSNI
NVTLGAHNIQRRENTQQHITARRAIRHPQYNQRTIQNDIMLLQLSRRVRRNRNVNPVALPRAQEGLRPGT
LCTVAGWGRVSMRRGTDTLREVQLRVQRDRQCLRIFGSYDPRRQICVGDRRERKAAFKGDSGGPLLCNNV
AHGIVSYGKSSGVPPEVFTRVSSFLPWIRTTMRSFKLLDQMETPL

B) SEQ ID NO:6

>gi|ref|NM_001911| cathepsin G [Homo sapiens]
```
        1 gcacagcagc aactgactgg gcagcctttc aggaaagatg cagccactcc tgcttctgct
       61 ggcctttctc ctacccactg gggctgaggc aggggagatc atcggaggcc gggagagcag
      121 gccccactcc cgcccctaca tggcgtatct tcagatccag agtccagcag gtcagagcag
      181 atgtggaggg ttcctggtgc gagaagactt tgtgctgaca gcagctcatt gctggggaag
      241 caatataaat gtcaccctgg gcgcccacaa tatccagaga cgggaaaaca cccagcaaca
      301 catcactgcg cgcagagcca tccgccaccc tcaatataat cagcggacca tccagaatga
      361 catcatgtta ttgcagctga gcagaagagt cagacggaat cgaaacgtga acccagtggc
      421 tctgcctaga gcccaggagg gactgagacc cgggacgctg tgcactgtgg ccggctgggg
      481 cagggtcagc atgaggaggg gaacagatac actccgagag gtgcagctga gagtgcagag
      541 ggataggcag tgcctccgca tcttcggttc ctacgacccc gaaggcaga tttgtgtggg
      601 ggaccggcgg gaacggaagg ctgccttcaa gggggattcc ggaggccccc tgctgtgtaa
      661 caatgtggcc cacggcatcg tctcctatgg aaagtcgtca ggggttcctc cagaagtctt
      721 caccagggtc tcaagtttcc tgccctggat aaggacaaca atgagaagct tcaaactgct
      781 ggatcagatg gagacccccc tgtgactgac tcttcttctc ggggacacag gccagctcca
      841 cagtgttgcc agagccttaa taaacgtcca cagagtataa ataaccaatt cctcatttgt
      901 tcattaaacg tcattcagta ctta
//
```

FIGURE 20

A) SEQ ID NO:7

>gi|6274552|ref|NP_009330.1| signal transducer and activator of transcription 1 isoform alpha [Homo sapiens]
MSQWYELQQLDSKFLEQVHQLYDDSFPMEIRQYLAQWLEKQDWEHAANDVSFATIRFHDLLSQLDDQYSR
FSLENNFLLQHNIRKSKRNLQDNFQEDPIQMSMIIYSCLKEERKILENAQRFNQAQSGNIQSTVMLDKQK
ELDSKVRNVKDKVMCIEHEIKSLEDLQDEYDFKCKTLQNREHETNGVAKSDQKQEQLLLKKMYLMLDNKR
KEVVHKIIELLNVTELTQNALINDELVEWKRRQQSACIGGPPNACLDQLQNWFTIVAESLQQVRQQLKKL
EELEQKYTYEHDPITKNKQVLWDRTFSLFQQLIQSSFVVERQPCMPTHPQRPLVLKTGVQFTVKLRLLVK
LQELNYNLKVKVLFDKDVNERNTVKGFRKFNILGTHTKVMNMEESTNGSLAAEFRHLQLKEQKNAGTRTN
EGPLIVTEELHSLSFETQLCQPGLVIDLETTSLPVVVISNVSQLPSGWASILWYNMLVAEPRNLSFFLTP
PCARWAQLSEVLSWQFSSVTKRGLNVDQLNMLGEKLLGPNASPDGLIPWTRFCKENINDKNFPFWLWIES
ILELIKKHLLPLWNDGCIMGFISKERERALLKDQQPGTFLLRFSESSREGAITFTWVERSQNGGEPDFHA
VEPYTKKELSAVTFPDIIRNYKVMAAENIPENPLKYLYPNIDKDHAFGKYYSRPKEAPEPMELDGPKGTG
YIKTELISVSEVHPSRLQTTDNLLPMSPEEFDEVSRIVGSVEFDSMMNTV

B) SEQ ID NO:8

>gi|ref| NM_007315| signal transducer and activator of transcription 1 isoform alpha [Homo sapiens]

```
    1 gctgagcgcg gagccgcccg gtgattggtg ggggcggaag ggggccgggc gccagcgctg
   61 ccttttctcc tgccgggtag tttcgctttc ctgcgcagag tctgcggagg ggctcgctg
  121 caccgggggg atcgcgcctg cagaccccca gaccgagcag aggcgaccca gcgcgctcgg
  181 gagaggctgc accgccgcgc ccccgcctag cccttccgga tcctgcgcgc agaaaagttt
  241 catttgctgt atgccatcct cgagagctgt ctaggttaac gttcgcactc tgtgtatata
  301 acctcgacag tcttggcacc taacgtgctg tgcgtagctg ctcctttggt tgaatcccca
  361 ggcccttgtt gggcacaag gtggcaggat gtctcagtgg tacgaacttc agcagcttga
  421 ctcaaaattc ctggagcagg ttcaccagct ttatgatgac agttttccca tggaaatcag
  481 acagtacctg gcacagtggt tagaaaagca agactgggag cacgctgcca atgatgtttc
  541 atttgccacc atccgttttc atgactcct gtcacagctg gatgatcaat atagtcgctt
  601 ttctttggag aataacttct gctacagca taacataagg aaaagcaagc gtaatcttca
  661 ggataatttt caggaagacc aatccagat gtctatgatc atttacagct gtctgaagga
  721 agaaaggaaa attctggaaa acgcccagag atttaatcag gctcagtcgg gaatattca
  781 gagcacagtg atgttagaca aacagaaga gcttgacagt aaagtcagaa atgtgaagga
  841 caaggttatg tgtatagagc atgaaatcaa gagcctggaa gatttacaag atgaatatga
  901 cttcaaatgc aaaaccttgc agaacagaga acacgagacc aatggtgtgg caaagagtga
  961 tcagaaacaa gaacagctgt tactcaagaa gatgtattta atgcttgaca taagagaaa
 1021 ggaagtagtt cacaaaataa tagagttgct gaatgtcact gaacttaccc agaatgccct
 1081 gattaatgat gaactagtgg agtggaagcg gagacagcag agcgcctgta ttgggggggcc
 1141 gcccaatgct tgcttggatc agctgcagaa ctggttcact atagttgcgg agagtctgca
 1201 gcaagttcgg cagcagctta aaaagttgga ggaattggaa cagaaataca cctacgaaca
 1261 tgaccctatc acaaaaaaca aacaagtgtt atgggaccgc acccttcagtc ttttccagca
 1321 gctcattcag agctcgtttg tggtggaaag acagccctgc atgccaacgc accctgcagag
 1381 gccgctggtc ttgaagacag gggtccagtt cactgtgaag ttgagactgt tggtgaaatt
 1441 gcaagagctg aattataatt tgaaagtcaa agtcttattt gataaagatg tgaatgagag
 1501 aaatacagta aaaggattta ggaagttcaa cattttgggc acgcacacaa aagtgatgaa
 1561 catggaggag tccaccaatg gcagtctggc ggctgaattt cggcacctgc aattgaaaga
 1621 acagaaaaat gctggcacca gaacgaatga gggtcctctc atcgttactg aagagcttca
 1681 ctcccttagt tttgaaaccc aattgtgcca gcctggtttg gtaattgacc tcgagacgac
 1741 ctctctgccc gttgtggtga tctccaacgt cagccagctc ccgagcggtt gggcctccat
 1801 cctttggtac aacatgctgg tggcggaacc caggaatctg tcctttcttcc tgactccacc
 1861 atgtgcacga tgggctcagc tttcagaagt gctgagttgg cagtttttctt ctgtcaccaa
 1921 aagaggtctc aatgtggacc agctgaacat gttgggagag aagcttcttg gtcctaacgc
 1981 cagcccgat ggtctcattc cgtggacgag gttttgtaag gaaaatataa atgataaaaa
 2041 ttttccttc tggctttgga ttgaaagcat cctaaaactc attaaaaaac acctgctccc
 2101 tctctggaat gatgggtgca tcatggcctt catcagcaag gagcgagagc gtgccctgtt
 2161 gaaggaccag cagccgggga ccttcctgct gcggttcagt gagagctccc gggaagggc
```

FIGURE 20 (CONTINUED)

```
2221 catcacattc acatgggtgg agcggtccca gaacggaggc gaacctgact tccatgcggt
2281 tgaaccctac acgaagaaag aactttctgc tgttactttc cctgacatca ttcgcaatta
2341 caaagtcatg gctgctgaga atattcctga gaatccoctg aagtatctgt atccaaatat
2401 tgacaaagac catgcctttg gaaagtatta ctccaggcca aaggaagcac cagagccaat
2461 ggaacttgat ggccctaaag gaactggata tatcaagact gagttgattt ctgtgtctga
2521 agttcaccct tctagacttc agaccacaga caacctgctc cccatgtctc ctgaggagtt
2581 tgacgaggtg tctcggatag tgggctctgt agaattcgac agtatgatga acacagtata
2641 gagcatgaat tttttcatc ttctctggcg acagttttcc ttctcatctg tgattccctc
2701 ctgctactct gttccttcac atcctgtgtt tctagggaaa tgaaagaaag gccagcaaat
2761 tcgctgcaac ctgttgatag caagtgaatt tttctctaac tcagaaacat cagttactct
2821 gaagggcatc atccatctta ctgaaggtaa aattgaaagg cattctctga agagtgggtt
2881 tcacaagtga aaaacatcca gatacaccca aagtatcagg acgagaatga gggtcctttg
2941 ggaaaggaga agttaagcaa catctagcaa atgttatgca taaagtcagt gcccaactgt
3001 tataggttgt tggataaatc agtggttatt tagggaactg cttgacgtag gaacggtaaa
3061 tttctgtggg agaattctta catgttttct ttgctttaag tgtaactggc agttttccat
3121 tggtttacct gtgaaatagt tcaaagccaa gtttatatac aattatatca gtcctctttc
3181 aaaggtagcc atcatggatc tggtaggggg aaaatgtgta ttttattaca tcttccacat
3241 tggctattta aagacaaaga caaattctgt ttcttgagaa gagaatatta gcttactgt
3301 ttgttatggc ttaatgacac tagctaatat caatagaagg atgtacattt ccaaattcac
3361 aagttgtgtt tgatatccaa agctgaatac attctgcttt catcttggtc acatacaatt
3421 atttttacag ttctcccaag ggagttaggc tattcacaac cactcattca aaagttgaaa
3481 ttaaccatag atgtagataa actcagaaat ttaattcatg tttcttaaat ggctactt
3541 gtcctttttg ttattagggt ggtatttagt ctattagcca caaaattggg aaaggagtag
3601 aaaaagcagt aactgacaac ttgaataata caccagagat aatatgagaa tcagatcatt
3661 tcaaaactca tttcctatgt aactgcattg agaactgcat atgtttcgct gatatatgtg
3721 ttttttcacat ttgcgaatgg ttccattctc tctccgtac ttttccaga cacttttttg
3781 agtggatgat gtttcgtgaa gtatactgta ttttaccctt tttccttcct tatcactgac
3841 acaaaaagta gattaagaga tgggtttgac aaggtcttc cctttacat actgctgtct
3901 atgtggctgt atcttgtttt tccactactg ctaccacaac tatattatca tgcaaatgct
3961 gtattcttct ttggtggaga taaagatttc ttgagttttg ttttaaaatt aaagctaaag
4021 tatctgtatt gcattaaata taatatgcac acagtgcttt ccgtggcact gcatacaatc
4081 tgaggcctcc tctctcagtt tttatataga tggcgagaac ctaagtttca gttgatttta
4141 caattgaaat gactaaaaaa caaagaagac aacattaaaa caatattgtt tctaattgct
4201 gaggtttagc tgtcagttct ttttgccctt tgggaattcg gcatggtttc attttactgc
4261 actagccaag agactttact tttaagaagt attaaaattc taaattcaa aaaaaaaaaa
4321 aaaaaa
```

METHOD OF INHIBITING PLATELET AGGREGATION AND CLOT FORMATION

RELATED APPLICATIONS

This application is a 35 U.S.C. §371 U.S. national entry of International Application PCT/US2008/007643 (WO 2008/156807) and claims the benefit of U.S. Provisional Application Ser. No. 60/936,229, filed Jun. 19, 2007, the entire contents of which are expressly incorporated herein by reference.

SEQUENCE LISTING

This application contains a Sequence Listing which has been submitted via EFS-Web and is hereby incorporated by reference in its entirety. Said ASCII copy, created on Feb. 1, 2012, is named 81822.txt, and is 26,591 bytes in size.

BACKGROUND OF THE INVENTION

Heart attack, stroke, and other vascular occlusive diseases (CVD) are the leading cause of morbidity and mortality in the United States, affecting nearly 20 million Americans. Because intravascular clot formation is known to play a prominent role in the occlusive events that characterize these diseases, current standard of care for both prevention and treatment of CVD involves either the chronic or transient use of one or more antithrombotic agents. Although these agents are effective, morbidity and mortality persist despite standard therapies. Inflammation is known to be an integral part of the vascular occlusive events that occur during heart attack and stroke, as well as those that occur after trauma, surgery, or percutaneous revascularization procedures. However, no therapies have yet been described that alleviate the inflammatory component of blood vessel occlusion because the specific inflammatory mechanism(s) that participate in clot formation have not previously been determined. New therapies that alleviate the inflammatory component of blood vessel occlusion and thereby vascular occlusive diseases are needed.

SUMMARY OF THE INVENTION

A large number of human diseases occur as a result of occlusion of arterial or venous blood vessels. Arterial and venous occlusions are known to occur through the interplay between cellular and soluble components contained within the vascular space. Although cellular and soluble components of the inflammatory system have been implicated in blood vessel occlusion, the specific inflammatory pathways that lead to vessel occlusion have not been determined. The instant invention is based, at least in part, on the discovery of the specific inflammatory cells and molecules that contribute to platelet activation and clot formation.

Accordingly, in one aspect, the invention provides methods of inhibiting platelet aggregation or clot formation in a subject, by inhibiting the activity or decreasing the amount of neutrophils in the subject, thereby inhibiting platelet aggregation or clot formation.

In one embodiment, inhibiting the activity or decreasing the amount of neutrophils in the subject is accomplished by inhibiting the activity or production of IL-6 or Interferon-gamma. In one embodiment, the subject is administered an inhibitor of Interferon-gamma activity or production. In another embodiment, the subject is administered an inhibitor of IL-6 activity or production.

In exemplary embodiments, the inhibitor is a nucleic acid, polypeptide, peptide, antibody, or small molecule. In specific embodiments, the IL-6 inhibitor is Am-80, madindoline A, madindoline B, 20S,21-Epoxy-resibufogenin-3-formate, or tocilizumab. In other embodiments, the Interferon gamma inhibitor is Secretory leucocyte protease inhibitor, Fontolizumab, or MD-1. In other embodiments, the inhibitor of IL-6 or Interferon-gamma is an inhibitor of STAT1 activity or expression.

In another embodiment, the subject has, or is at risk of developing, a vascular occlusive disease, an ischemia or reperfusion injury, an acute or chronic inflammatory state, autoimmune disease, myelodysplastic syndrome, tissue injury from surgery or accidental trauma, acute bacterial or viral infection, has undergone a microvascular surgical reconstructive procedure, is receiving granulocyte colony stimulating factor therapy, receiving stem cell therapy, or has sickle cell anemia.

In one embodiment, the subject has an acute or chronic inflammatory state as defined by: peripheral blood total leukocyte count $>7\times10^3/\mu l$; peripheral blood neutrophil count $>4\times10^3/\mu l$; or, plasma IL-6 concentration $>3$ pg/ml.

In one embodiment, the autoimmune disease is Rheumatoid Arthritis, Systemic Lupus Erythematosis, Sjogren's Disease, or Scleroderma.

In another embodiment, the myelodysplastic syndrome is acute myelogenous leukemia, or chronic myelogenous leukemia.

In another embodiment, the tissue injury is from surgery or accidental trauma.

In another embodiment, the acute bacterial or viral infection is pneumonia, bronchitis, urinary tract infection, or sepsis.

In another embodiment, wherein the subject has had a microvascular surgical reconstructive procedure.

In another embodiment, the subject is receiving granulocyte colony stimulating factor therapy before or after a bone marrow transplant, or for mobilization of peripheral stem cells.

In another embodiment, the vascular occlusive disease is a heart attack, myocardial infarction, unstable angina, stroke, peripheral arterial occlusive disease, thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

In another embodiment, the ischemia/reperfusion injury is due to administration of fibrinolytic therapy to an occluded cerebral, coronary, or peripheral artery; balloon angioplasty or arterecteomy/atherectomy of a cerebral, coronary, or peripheral artery; or, clamping of the aorta or major organ vessel during surgery.

In another embodiment, aspirin therapy is likely to fail or has already failed to prevent aggregation or clot formation in the subject.

In another aspect, the invention provides methods of inhibiting platelet aggregation or clot formation in a subject, by inhibiting the expression or activity of cathepsin G in the subject; thereby inhibiting platelet aggregation or clot formation.

In one embodiment, wherein the cathepsin G is produced by neutrophils. In another embodiment, inhibiting the expression or activity of cathepsin G comprises administering the subject an inhibitor selected from the group consisting of a nucleic acid, polypeptide, peptide, antibody, or small molecule.

In exemplary embodiments, the inhibitor of cathepsin G is Z-gly-leu-phe-chloromethyl ketone, cathepsin G inhibitor 1 ($C_{36}H_{33}N_2O_6P$), Gly-Leu-Phe, benzyloxycarbonyl-Gly-Leu-Phe-chloromethyl ketone, Ala-Ala-Pro-Phe (SEQ ID NO: 9), N-(Methoxysuccinyl)-Ala-Ala-Pro-Phe-chloromethyl ketone (SEQ ID NO: 10), Ala-Ala-Pro-Val (SEQ ID NO: 11), N-(Methoxysuccinyl)-Ala-Ala-Pro-Val-chloromethyl ketone (SEQ ID NO: 12), Acetyl-Thr-Glu-Phe-Gly-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-Gly-OH (acetyl-eglin C) (SEQ ID NO: 13), Pro-Val-Thr-Leu (SEQ ID NO: 14), Ser-Pro-Val-Thr-Leu-Asp-Leu-Arg-Tyr (SEQ ID NO: 15), monocyte neutrophil elastase inhibitor, maspin, secretory leukocyte protease inhibitor, Gly-Thr-Glu-Ala-Ala-Ala-Ala-Thr-Ala-Gly-Ile-Ala-Thr-Phe-Cys (SEQ ID NO: 16), Met-Leu-Met-Phe-Glu-Glu-Asn-Phe-Thr-Ala-Asp-His-Pro-Phe (SEQ ID NO: 17), Gly-Thr-Glu-Ala-Ala-Ala-Ala-Thr-Gly-Gly-Ile-Ala-Thr-Phe-Cys (SEQ ID NO: 18), Met-Leu-Leu-Pro-Glu-Glu-Glu-Phe-Thr-Val-Asp-His-Pro-Phe (SEQ ID NO: 19), Gly-Thr-Glu-Ala-Ala-Ala-Ala-Thr-Gly-Gly-Ile-Ile-Gln-Val-Leu-Cys-Glu-Lys-Met-Pro-Thr-Pro-Gln-Glu-Val-Phe-Thr-Val-Asp-His-Pro-Phe (SEQ ID NO: 20), β-ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3, or Ac-Ala-Ala-ANle-OEt.

In one embodiment, the inhibitor of cathepsin G expression is an inhibitor of IL-6 activity or expression. In one embodiment, the inhibitor of cathepsin G expression is an inhibitor of Interferon gamma activity or expression. In specific embodiments, the inhibitor of cathepsin G expression is an inhibitor of STAT1 activity or expression.

In certain embodiments, the subject has, or is at risk of developing, a vascular occlusive disease. In another embodiment the subject has, or is at risk of experiencing an ischemia or reperfusion injury. In another embodiment the subject has an acute or chronic inflammatory state comprising a peripheral blood total leukocyte count >$7\times10^3$/μl; a peripheral blood neutrophil count >~$4\times10^3$/μl; or, a plasma IL-6 concentration >3 pg/ml.

In another embodiment, the subject has an autoimmune disease selected from the group consisting of Rheumatoid Arthritis, SLE, Sjogren's Disease, and Scleroderma.

In another embodiment, the subject has a myelodysplastic syndrome selected from the group consisting of acute myelogenous leukemia, and chronic myelogenous leukemia. In another embodiment, the subject has experienced tissue injury from surgery or accidental trauma. In another embodiment, the subject has an acute bacterial or viral infection selected from the group consisting of pneumonia, bronchitis, urinary tract infection, and sepsis. In another embodiment, the subject has undergone a microvascular surgical reconstructive procedure.

In specific embodiments, the subject is receiving granulocyte colony stimulating factor therapy, stem cell therapy, or has sickle cell anemia.

In another embodiment, the vascular occlusive disease is a heart attack, myocardial infarction, unstable angina, stroke, peripheral arterial occlusive disease or thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

In another embodiment, the ischemia or reperfusion injury is due to administration of fibrinolytic therapy to treat an occluded cerebral, coronary, or peripheral artery; balloon angioplasty or arterecteomy/atherectomy of a cerebral, coronary, or peripheral artery; or clamping of the aorta or major organ vessel during surgery.

In a related embodiment, aspirin therapy is likely to fail or has already failed to prevent aggregation or clot formation in the subject.

In another aspect, the invention provides methods of inhibiting the activity of neutrophils in a subject, by inhibiting the activity or expression of IL-6, thereby inhibiting the activity of neutrophils in a subject.

In one embodiment, the subject is administered an IL-6 inhibitor. In exemplary embodiments, the inhibitor is a nucleic acid, polypeptide, peptide, antibody, or small molecule. Exemplary IL-6 inhibitors are Am-80, madindoline A, madindoline B, 20S,21-Epoxy-resibufogenin-3-formate, and tocilizumab.

In another aspect, the invention provides methods of inhibiting the activity of neutrophils in a subject, by inhibiting the activity or expression of Interferon-gamma, thereby inhibiting the activity of neutrophils in a subject. In one embodiment, the subject is administered an Interferon-gamma inhibitor. In exemplary embodiments, the interferon-gamma inhibitor is a nucleic acid, polypeptide, peptide, antibody, or small molecule. Exemplary inhibitors include Secretory leucocyte protease inhibitor, Fontolizumab, and the MD-1 antibody.

In another aspect, the invention provides methods of inhibiting the activity of neutrophils in a subject, by inhibiting the activity or expression of STAT1-alpha, thereby inhibiting the activity of neutrophils in a subject. In one embodiment, the subject is administered a STAT1-alpha inhibitor. In exemplary embodiments, the interferon-gamma inhibitor is a nucleic acid, polypeptide, peptide, antibody, or small molecule. Exemplary inhibitors include parthenolide or STAT1-beta.

In certain embodiments, the subject has, or is at risk of developing, a vascular occlusive disease, an ischemia or reperfusion injury, an acute or chronic inflammatory state, an autoimmune disease, a myelodysplastic syndrome, a tissue injury from surgery or accidental trauma, an acute bacterial or viral infection, has undergone a microvascular surgical reconstructive procedure, is receiving granulocyte colony stimulating factor therapy, receiving stem cell therapy, or has sickle cell anemia.

In related embodiments, the subject has an acute or chronic inflammatory state as defined by: peripheral blood total leukocyte count >$7\times10^3$/μl; peripheral blood neutrophil count >$4\times10^3$/μl; or, plasma IL-6 concentration >3 pg/ml.

In related embodiments, the autoimmune disease is Rheumatoid Arthritis, Systemic Lupus Erythematosis, Sjogren's Disease, or Scleroderma.

In another related embodiment, the myelodysplastic syndrome is acute myelogenous leukemia, or chronic myelogenous leukemia.

In another related embodiment, the tissue injury from surgery or accidental trauma occurred within the past 6 months.

In another related embodiment, the acute bacterial or viral infection is pneumonia, bronchitis, urinary tract infection, or sepsis.

In another related embodiment, the microvascular surgical reconstructive procedure occurred within the past 30 days.

In another related embodiment, the subject is receiving granulocyte colony stimulating factor therapy before or after a bone marrow transplant, or for mobilization of peripheral stem cells.

In specific embodiments, the vascular occlusive disease is a heart attack, myocardial infarction, unstable angina, stroke, peripheral arterial occlusive disease, thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

In another embodiment, the ischemia or reperfusion injury is due to administration of fibrinolytic therapy to treat an occluded cerebral, coronary, or peripheral artery; a balloon angioplasty or arterecteomy/atherectomy of a cerebral, coronary, or peripheral artery; or, clamping of the aorta or major organ vessel during surgery.

In another aspect, the invention provides methods of treating a subject having, or at risk of developing, a vascular occlusive disease by administering to the subject an effective amount of a compound that inhibits the expression or activity of IL-6, thereby treating the subject.

In one embodiment, the inhibitor is a nucleic acid, polypeptide, peptide, antibody, or small molecule. Exemplary inhibitors include Am-80, madindoline A, madindoline B, 20S,21-Epoxy-resibufogenin-3-formate, or tocilizumab.

In another aspect, the invention provides methods of treating a subject having, or at risk of developing, a vascular occlusive disease by administering to the subject an effective amount of a compound that inhibits the expression or activity of Interferon-gamma, thereby treating the subject.

In one embodiment, the inhibitor is a nucleic acid, polypeptide, peptide, antibody, or small molecule. Exemplary inhibitors include Secretory leucocyte protease inhibitor, Fontolizumab, or MD-1.

In another aspect, the invention provides methods of treating a subject having, or at risk of developing, a vascular occlusive disease by administering to the subject an effective amount of a compound that inhibits the expression or activity of STAT1-alpha, thereby treating the subject.

In one embodiment, the inhibitor is a nucleic acid, polypeptide, peptide, antibody, or small molecule. Exemplary inhibitors include the STAT1-alpha inhibitor is parthenolide or STAT1-beta.

In another aspect, the invention provides methods of treating a subject having, or at risk of developing a vascular occlusive disease by administering to the subject an effective amount of a compound that inhibits the expression or activity of capthesin G, thereby treating the subject.

In one embodiment, the inhibitor is a nucleic acid, polypeptide, peptide, antibody, or small molecule. Exemplary inhibitors include Z-gly-leu-phe-chloromethyl ketone, cathepsin G inhibitor 1 ($C_{36}H_{33}N_2O_6P$), Gly-Leu-Phe, benzyloxycarbonyl-Gly-Leu-Phe-chloromethyl ketone, AlaAla-Pro-Phe (SEQ ID NO: 9), N-(Methoxysuccinyl)-Ala-Ala-Pro-Phe-chloromethyl ketone (SEQ ID NO: 10), Ala-Ala-Pro-Val (SEQ ID NO: 11), N-(Methoxysuccinyl)-Ala-Ala-Pro-Val-chloromethyl ketone (SEQ ID NO: 12), Acetyl-Thr-Glu-Phe-Gly-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-Gly-OH (acetyl-eglin C) (SEQ ID NO: 13), Pro-Val-Thr-Leu (SEQ ID NO: 14), Ser-Pro-Val-Thr-Leu-Asp-Leu-Arg-Tyr (SEQ ID NO: 15), monocyte neutrophil elastase inhibitor, maspin, secretory leukocyte protease inhibitor, Gly-Thr-Glu-Ala-Ala-Ala-Ala-Thr-Ala-Gly-Ile-Ala-Thr-Phe-Cys (SEQ ID NO: 16), Met-Leu-Met-Phe-Glu-Glu-Asn-Phe-Thr-Ala-Asp-His-Pro-Phe (SEQ ID NO: 17), Gly-Thr-Glu-Ala-Ala-Ala-Ala-Thr-Gly-Gly-Ile-Ala-Thr-Phe-Cys (SEQ ID NO: 18), Met-Leu-Leu-Pro-Glu-Glu-Glu-Phe-Thr-Val-Asp-His-Pro-Phe (SEQ ID NO: 19), Gly-Thr-Glu-Ala-Ala-Ala-Ala-Thr-Gly-Gly-Ile-Ile-Gln-Val-Leu-Cys-Glu-Lys-Met-Pro-Thr-Pro-Gln-Glu-Val-Phe-Thr-Val-Asp-His-Pro-Phe (SEQ ID NO: 20), —ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3, or Ac-Ala-Ala-ANle-OEt In related embodiments, the methods of the invention further comprise the step of identifying individuals that have, or are at risk of developing a vascular occlusive disease.

In other related embodiments, the methods of the invention are used in subjects in which aspirin treatment is likely to fail or has already failed to treat a vascular occlusive disease.

In specific embodiments, the vascular occlusive disease is a heart attack, myocardial infarction, unstable angina, stroke, peripheral arterial occlusive disease or thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

In another aspect, the invention provides methods of treating a subject having, or at risk of developing, a disease or disorder characterized by platelet aggregation by administering to the subject an effective amount of a compounds that inhibits the expression or activity of capthesin G, thereby treating the subject.

In certain embodiments, the inhibitor is a nucleic acid, polypeptide, peptide, antibody, or a small molecule. Exemplary inhibitors include Z-gly-leu-phe-chloromethyl ketone, cathepsin G inhibitor 1 ($C_{36}H_{33}N_2O_6P$), Gly-Leu-Phe, benzyloxycarbonyl-Gly-Leu-Phe-chloromethyl ketone, Ala-Ala-Pro-Phe (SEQ ID NO: 9), N-(Methoxysuccinyl)-Ala-Ala-Pro-Phe-chloromethyl ketone (SEQ ID NO: 10), Ala-Ala-Pro-Val (SEQ ID NO: 11), N-(Methoxysuccinyl)-Ala-Ala-Pro-Val-chloromethyl ketone (SEQ ID NO: 12), Acetyl-Thr-Glu-Phe-Gly-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-Gly-OH (acetyl-eglin C) (SEQ ID NO: 13), Pro-Val-Thr-Leu (SEQ ID NO: 14), Ser-Pro-Val-Thr-Leu-Asp-Leu-Arg-Tyr (SEQ ID NO: 15), monocyte neutrophil elastase inhibitor, maspin, secretory leukocyte protease inhibitor, Gly-Thr-Glu-Ala-Ala-Ala-Ala-Thr-Ala-Gly-Ile-Ala-Thr-Phe-Cys (SEQ ID NO: 16), Met-Leu-Met-Phe-Glu- Glu-Asn-Phe-Thr-Ala-Asp-His-Pro-Phe (SEQ ID NO: 17), Gly-Thr-Glu-Ala-Ala-Ala-Ala-Thr-Gly-Gly-Ile-Ala-Thr-Phe-Cys (SEQ ID NO: 18), Met-Leu-Leu-Pro-Glu-Glu-Glu-Phe-Thr-Val-Asp-His-Pro-Phe (SEQ ID NO: 19), Gly-Thr-Glu-Ala-Ala-Ala-Ala-Thr-Gly-Gly-Ile-Ile-Gln-Val-Leu-Cys-Glu-Lys-Met-Pro-Thr-Pro-Gln-Glu-Val-Phe-Thr-Val-Asp-His-Pro-Phe (SEQ ID NO: 20), β-ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3, or Ac-Ala-Ala-ANle-OEt In another aspect, the invention provides methods of treating a subject having, or at risk of developing, a disease or disorder characterized by platelet aggregation by administering to the subject an effective amount of a compound that inhibits the expression or activity of IL-6, thereby treating the subject.

In one embodiment, the inhibitor is a nucleic acid, polypeptide, peptide, antibody, or small molecule. Exemplary inhibitors include Am-80, madindoline A, madindoline B, 20S,21-Epoxy-resibufogenin-3-formate, or tocilizumab.

In another aspect, the invention provides methods of treating a subject having, or at risk of developing, a disease or disorder characterized by platelet aggregation by administering to the subject an effective amount of a compound that inhibits the expression or activity of Interferon-gamma, thereby treating the subject.

In one embodiment, the inhibitor is a nucleic acid, polypeptide, peptide, antibody, or small molecule. Exemplary inhibitors include Secretory leucocyte protease inhibitor, Fontolizumab, or MD-1.

In another aspect, the invention provides methods of treating a subject having, or at risk of developing, a disease or disorder characterized by platelet aggregation by administering to the subject an effective amount of a compound that inhibits the expression or activity of STAT1-alpha, thereby treating the subject.

In one embodiment, the inhibitor is a nucleic acid, polypeptide, peptide, antibody, or small molecule. Exemplary inhibitors include parthenolide or STAT1beta.

In another aspect, the invention provides methods for diagnosing the presence of a vascular occlusive disease comprising measuring the amount or activity of cathepsin G in serum, plasma, or leukocytes, wherein an increased amount or activity as compared to a control is indicative of an increased risk of developing a vascular occlusive disease.

In related embodiments, the vascular occlusive disease is a heart attack, myocardial infarction, unstable angina, stroke, peripheral arterial occlusive disease, thromboembolism, or venous thromboembolism In another aspect, the invention provides methods for determining the likelihood of a subject developing a vascular occlusive disease comprising measuring the amount or activity of cathepsin G in serum, plasma, or leukocytes, wherein an increased amount or activity as compared to a control is indicative of an increased risk of developing a vascular occlusive disease.

In related embodiments, the vascular occlusive disease is a heart attack, myocardial infarction, unstable angina, stroke, peripheral arterial occlusive disease, thromboembolism, or venous thromboembolism In another aspect, the invention provides methods for diagnosing the presence of a vascular occlusive disease comprising measuring the amount or activity of interferon-gamma in serum, plasma, or leukocytes, wherein an increased amount or activity as compared to a control is indicative of an increased risk of developing a vascular occlusive disease.

In related embodiments, the vascular occlusive disease is a heart attack, myocardial infarction, unstable angina, stroke, peripheral arterial occlusive disease, thromboembolism, or venous thromboembolism In another aspect, the invention provides methods for determining the likelihood of a subject developing a vascular occlusive disease comprising measuring of the amount or activity of interferon-gamma in serum, plasma, or leukocytes, wherein an increased amount or activity as compared to a control is indicative of an increased risk of developing a vascular occlusive disease.

In related embodiments, the vascular occlusive disease is a heart attack, myocardial infarction, unstable angina, stroke, peripheral arterial occlusive disease, thromboembolism, or venous thromboembolism In another aspect, the invention provides kits for the prevention or treatment of a vascular occlusive disease comprising a capthesin G inhibitor and instructions for use.

In another aspect, the invention provides kits for the prevention or treatment of a vascular occlusive disease comprising an IL-6 inhibitor and instructions for use. In exemplary embodiments, the IL-6 inhibitor is Am-80, madindoline A, madindoline B, 20S,21-Epoxy-resibufogenin-3-formate, or tocilizumab.

In another aspect, the invention provides kits for the prevention or treatment of a vascular occlusive disease comprising an Interferon-gamma inhibitor and instructions for use. In exemplary embodiments, the Interferon-gamma inhibitor is Secretory leucocyte protease inhibitor, Fontolizumab, or MD-1.

In another aspect, the invention provides kits for the prevention or treatment of a vascular occlusive disease comprising a STAT1-alpha inhibitor and instructions for use.

In exemplary embodiments, the STAT1-alpha inhibitor is parthenolide or STAT1-beta.

were isolated by histopaque centrifugation and cultured in RPMI/5% human serum for 24 hours in the presence and absence of IL-6 (10 ng/ml), INFγ (10 ng/ml), and parthenolide (PAR, 5 μM). Neutrophils were reconstituted with freshly prepared platelet rich plasma, and impedance aggregometry (in response to 15 μM TRAP) was assessed in the absence and presence of PMNs treated as shown. A. IL-6 treatment, N=8. B. INFγ treatment, N=6. *P<0.05 vs. −PMN, **P<0.01 vs. all other conditions within group by Bonferroni corrected post hoc test.

Figure 16:
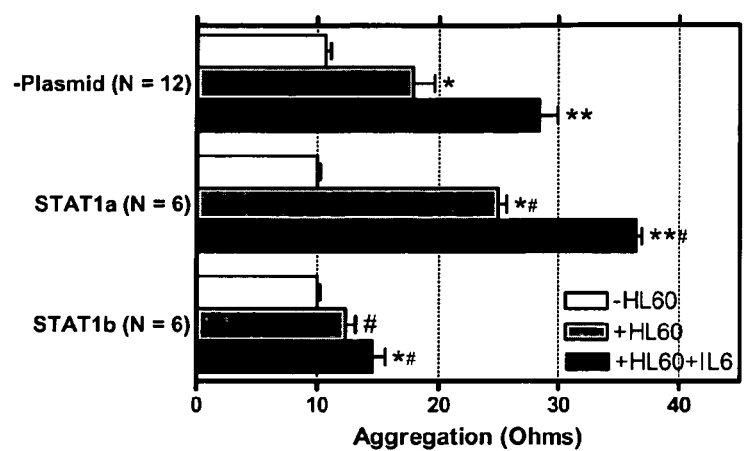

FIG. 16 demonstrates that STAT1α mediates the pro-aggregatory effect of neutrophilic cells and IL-6. Native HL60 cells and STAT1α and STAT1β transfectants were treated with 1.5% DMSO for 96 hours to induce neutrophil differentiation. Cells were exposed to IL-6/vehicle (10 ng/ml) during the terminal 48 hours of differentiation. HL60 cells were harvested and reconstituted with platelet rich plasma and aggregation in response to TRAP (15 μM) recorded. P<0.0001 for main effect of HL60 cells for −Plasmid and STAT1a; P=0.02 for main effect of HL60 cells for STAT1b. *P<0.05 vs. −HL60, P<0.01 vs. −HL60 and +HL60 within experimental condition by Bonferroni post hoc test; #P<0.05 vs. −Plasmid control for analogous cell treatment condition across experiments by Dunnett's post-hoc test.

FIGS. 17A and B set for the protein and nucleic acid sequences of IL6 (SEQ ID NOs: 1 and 2), respectively.

FIGS. 18A and B set for the protein and nucleic acid sequences of INFγ, (SEQ ID NOs: 3 and 4), respectively.

FIGS. 19A and B set for the protein and nucleic acid sequences of cathepsin G (SEQ ID NOs: 5 and 6), respectively.

FIGS. 20A and B set for the protein and nucleic acid sequences of STAT1 (SEQ ID NOs: 7 and 8), respectively.

DETAILED DESCRIPTION OF THE INVENTION

A large number of human diseases occur as a result of occlusion of arterial or venous blood vessels. Arterial and venous occlusions are known to occur through the interplay between cellular and soluble components contained within the vascular space. Although cellular and soluble components of the inflammatory system have been implicated in blood vessel occlusion, the specific inflammatory pathways that lead to vessel occlusion have not been determined. The instant invention is based, at least in part, on the discovery of the specific inflammatory cells and molecules that contribute to platelet activation, clot formation and cardiovascular disease.

The instant invention provides methods and compositions for treating a subject having any one of a number of diseases, disorders or conditions that result, or are modulated by, the interaction of the molecules identified herein as being involved in platelet activation and/or clot formation.

Specifically, the instant invention provides methods and compositions for modulating the activity or expression or neutrophils and/or cathepsin G. Moreover, the invention provides methods and compositions for modulating neutrophils and/or cathepsin G by decreasing the expression or activity of interleukin 6 (IL-6), interferon γ (INFγ) or STAT1. The modulation of the activity or expression of cellular proteins can be modulated by a number of art recognized methods such as those set forth below.

Molecules of the Invention

The instant invention provides methods and compositions for modulating the activity or expression of neutrophils by modulating, for example, the activity or expression of IL6, INFγ, cathepsin G, or STAT1.

Interleukin 6 (IL-6) is a cytokine secreted by T cells and macrophages to stimulate immune response. The polypeptide and nucleic acid sequences are set forth as SEQ ID NO: 1 and 2, respectively.

Interferon-gamma (IFNγ) coordinates a diverse array of cellular programs through transcriptional regulation of immunologically relevant genes The polypeptide and nucleic acid sequences of INFγ are set forth as SEQ ID NO: 3 and 4, respectively.

Cathepsin G is serine protease produced in specialized azurophil granules of neutrophilic polymorphonuclear leukocytes and is described in Maison et al. J. Immunol. 147 (3), 921-926 (1991). The polypeptide and nucleic acid sequences of INFγ are set forth as SEQ ID NO: 5 and 6, respectively.

STAT1 alpha is a member of the Signal Transducers and Activators of Transcription family of transcription factors. The polypeptide and nucleic acid sequences of INFγ are set forth as SEQ ID NO: 7 and 8, respectively.

As used herein, "Granulocyte colony-stimulating factor (G-CSF)" refers to a blood growth factor that stimulates the bone marrow to produce neutrophils. The sequence of G-CSF nucleotide sequence is set forth as Genebank Accession number NM_000759 and the polypeptide is set forth as Genebank Accession number NP_000750. Also see, for example, Nagata et al. (EMBO J. 5 (3), 575-581 (1986)).

"Fragments" or "biologically active portions" include polypeptide fragments suitable for use as immunogens to raise antibodies or for use in screening assays to identify modulators of the activity of a protein. Fragments include peptides comprising amino acid sequences sufficiently identical to or derived from the amino acid sequence of a protein, or partial-length protein, of the invention and exhibiting at least one activity of the protein, but which include fewer amino acids than the full-length. Typically, biologically active portions comprise a domain or motif with at least one activity of the protein. A biologically active portion of a polypeptide can be a fragment which is, for example, 10, 25, 50, 100 or more amino acids in length.

Antibodies

The invention provides antibodies to the identified polypeptides, e.g., IL6, INFγ, cathepsin G, or STAT1. In a preferred embodiment, the antibodies modulate, e.g., inhibit, the expression or activity of the proteins. An isolated polypeptide of the invention can be used as an immunogen to generate antibodies that bind proteins using standard techniques for polyclonal and monoclonal antibody preparation. A full-length protein can be used or, alternatively, the invention provides antigenic peptide fragments of proteins for use as immunogens. The antigenic peptide of a protein comprises at least 8, preferably 10, 15, 20, or amino acid residues of the amino acid sequence shown in SEQ ID NO:2 and encompasses an epitope of a protein such that an antibody raised against the peptide forms a specific immune complex with the protein. Preferred epitopes encompassed by the antigenic peptide are regions of a protein that are located on the surface of the protein, e.g., hydrophilic regions.

Accordingly, another aspect of the invention pertains to polyclonal and monoclonal antibodies that bind a protein identified herein, e.g., IL6, INFγ, cathepsin G, or STAT1. Polyclonal antibodies can be prepared by immunizing a suitable subject (e.g., rabbit, goat, mouse, or other mammal) with an immunogen. The antibody titer in the immunized subject can be monitored over time by standard techniques, such as with an enzyme linked immunosorbent assay (ELISA) using immobilized protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), the EBV-hybridoma technique (Cole et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan et al., eds. (1994) Current Protocols in Immunology (John Wiley & Sons, Inc., New York, N.Y.); Galfre et al. (1977) Nature 266:55052; Kenneth (1980) in Monoclonal Antibodies: A New Dimension In Biological Analyses (Plenum Publishing Corp., NY; and Lerner (1981) Yale J. Biol. Med., 54:387-402).

Alternative to preparing monoclonal antibody-secreting hybridomas, a monoclonal antibody can be identified and isolated by screening a recombinant combinatorial immunoglobulin library (e.g., an antibody phage display library) with a protein to thereby isolate immunoglobulin library members that bind the protein. Kits for generating and screening phage display libraries are commercially available (e.g., the Pharmacia Recombinant Phage Antibody System, Catalog No. 27-9400-01; and the Stratagene SurfZap τ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Additionally, recombinant antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125, 023, and 173,494; U.S. Pat. Nos. 4,816,567 and 5,225,539; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) Bio/Techniques 4:214; Jones et al. (1986) Nature 321:552-525; Verhoeyan et al. (1988) Science 239:1534; and Beidler et al. (1988) J. Immunol. 141:4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65-93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

In one particular embodiment, the methods of the instant invention use the humanized anti-INFγ antibody Fontolizumab (Biogen Idec, Cambridge, Mass.) or the MD-1 antibody (eBioscience, Inc, San Diego, Calif.). In another embodiment, the methods of the instant invention use the humanized anti-IL6 antibody tocilizumab (Roche, Basel, Switzerland).

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899-903).

Antisense Molecules

In one embodiment, the invention provides inhibitors of, for example, IL6, INFγ, cathepsin G, or STAT1 that are antisense molecules. Antisense molecules as used herein include antisense or sense oligonucleotides comprising a single-stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

RNAi

RNA interference refers to the process of sequence-specific post transcriptional gene silencing in animals mediated by short interfering RNAs (siRNA) (Fire et al., Nature, 391, 806 (1998)). The corresponding process in plants is referred to as post transcriptional gene silencing or RNA silencing and is also referred to as quelling in fungi. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L. (reviewed in Sharp, P. A., RNA interference-2001, Genes & Development 15:485-490 (2001)).

Small interfering RNAs (siRNAs) are powerful sequence-specific reagents designed to suppress the expression of genes in cultured mammalian cells through a process known as RNA interference (RNAi). Elbashir, S. M. et al. Nature 411:494-498 (2001); Caplen, N. J. et al. Proc. Natl. Acad. Sci. USA 98:9742-9747 (2001); Harborth, J. et al. J. Cell Sci. 114:4557-4565 (2001). The term "short interfering RNA" or "siRNA" refers to a double stranded nucleic acid molecule capable of RNA interference "RNAi", (see Kreutzer et al., WO 00/44895; Zernicka-Goetz et al. WO 01/36646; Fire, WO 99/32619; Mello and Fire, WO 01/29058). As used herein, siRNA molecules are limited to RNA molecules but further encompasses chemically modified nucleotides and non-nucleotides. siRNA gene-targeting experiments have been carried out by transient siRNA transfer into cells (achieved by such classic methods as liposome-mediated transfection, electroporation, or microinjection).

Molecules of siRNA are 21- to 23-nucleotide RNAs, with characteristic 2- to 3-nucleotide 3'-overhanging ends resembling the RNase III processing products of long double-stranded RNAs (dsRNAs) that normally initiate RNAi. When introduced into a cell, they assemble with yet-to-be-identified proteins of an endonuclease complex (RNA-induced silencing complex), which then guides target mRNA cleavage. As a consequence of degradation of the targeted mRNA, cells with a specific phenotype characteristic of suppression of the corresponding protein product are obtained. The small size of siRNAs, compared with traditional antisense molecules, prevents activation of the dsRNA-inducible interferon system present in mammalian cells. This avoids the nonspecific phenotypes normally produced by dsRNA larger than 30 base pairs in somatic cells.

Intracellular transcription of small RNA molecules is achieved by cloning the siRNA templates into RNA polymerase III (Pol III) transcription units, which normally encode the small nuclear RNA (snRNA) U6 or the human RNase P RNA H1. Two approaches have been developed for expressing siRNAs: in the first, sense and antisense strands constituting the siRNA duplex are transcribed by individual promoters (Lee, N. S. et al. Nat. Biotechnol. 20, 500-505 (2002). Miyagishi, M. & Taira, K. Nat. Biotechnol. 20, 497-500 (2002); in the second, siRNAs are expressed as fold-back stem-loop structures that give rise to siRNAs after intracellular processing (Paul, C. P. et al. Nat. Biotechnol. 20:505-508 (2002)). The endogenous expression of siRNAs from introduced DNA templates is thought to overcome some limitations of exogenous siRNA delivery, in particular the transient loss of phenotype. U6 and H1 RNA promoters are members of the type III class of Pol III promoters. (Paule, M. R. & White, R. J. Nucleic Acids Res. 28, 1283-1298 (2000)).

Co-expression of sense and antisense siRNAs mediate silencing of target genes, whereas expression of sense or antisense siRNA alone do not greatly affect target gene expression. Transfection of plasmid DNA, rather than synthetic siRNAs, may appear advantageous, considering the danger of RNase contamination and the costs of chemically synthesized siRNAs or siRNA transcription kits. Stable expression of siRNAs allows new gene therapy applications, such as treatment of persistent viral infections. Considering the high specificity of siRNAs, the approach also allows the targeting of disease-derived transcripts with point mutations, such as RAS or TP53 oncogene transcripts, without alteration of the remaining wild-type allele. Finally, by high-throughput sequence analysis of the various genomes, the DNA-based methodology may also be a cost-effective alternative for automated genome-wide loss-of-function phenotypic analysis, especially when combined with miniaturized array-based phenotypic screens. (Ziauddin, J. & Sabatini, D. M. Nature 411:107-110 (2001)).

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409:363 (2001)). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., Science, 293, 834 (2001)). The RNAi response also features an endonuclease complex containing a siRNA, commonly referred to as an RNA-induced silencing complex (RISC), which mediates cleavage of single stranded RNA having sequence homologous to the siRNA. Cleavage of the target RNA takes place in the middle of the region complementary to the guide sequence of the siRNA duplex (Elbashir et al., Genes Dev., 15, 188 (2001)).

This invention provides an expression system comprising an isolated nucleic acid molecule comprising a sequence capable of specifically hybridizing to the CA sequences. In an embodiment, the nucleic acid molecule is capable of inhibiting the expression of the CA protein. A method of inhibiting expression of CA inside a cell by a vector-directed expression of a short RNA which short RNA can fold in itself and create a double strand RNA having CA mRNA sequence identity and able to trigger posttranscriptional gene silencing, or RNA interference (RNAi), of the CA gene inside the cell. In another method a short double strand RNA having CA mRNA sequence identity is delivered inside the cell to trigger posttranscriptional gene silencing, or RNAi, of the CA gene. In various embodiments, the nucleic acid molecule is at least a 7 mer, at least a 10 mer, or at least a 20 mer. In a further embodiment, the sequence is unique.

MicroRNA

The term "miRNA" is used according to its ordinary and plain meaning and refers to a microRNA molecule found in eukaryotes that is involved in RNA-based gene regulation. The term will be used to refer to the single-stranded RNA molecule processed from a precursor. Individual miRNAs have been identified and sequenced in different organisms, and they have been given names. Names of miRNAs and their sequences are provided herein. Additionally, other miRNAs are known to those of skill in the art and can be readily implemented in embodiments of the invention. The methods and compositions should not be limited to miRNAs identified in the application, as they are provided as examples, not necessarily as limitations of the invention.

MicroRNA molecules ("miRNAs") are generally 21 to 22 nucleotides in length, though lengths of 17 and up to 25 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals. Dicer is ribonuclease III-like nuclease. The processed miRNA is typically a portion of the stem.

The processed miRNA (also referred to as "mature miRNA") become part of a large complex to down-regulate a particular target gene. Examples of animal miRNAs include those that imperfectly basepair with the target, which halts translation. SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target.

The present invention concerns, in some embodiments of the invention, short nucleic acid molecules that function as miRNAs or as inhibitors of miRNA in a cell. The term "short" refers to a length of a single polynucleotide that is 150 nucleotides or fewer. The nucleic acid molecules are synthetic. The term "synthetic" means the nucleic acid molecule is isolated and not identical in sequence (the entire sequence) and/or chemical structure to a naturally-occurring nucleic acid molecule, such as an endogenous precursor miRNA molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together.

It is understood that a "synthetic nucleic acid" of the invention means that the nucleic acid does not have a chemical structure or sequence of a naturally occurring nucleic acid. Consequently, it will be understood that the term "synthetic miRNA" refers to a "synthetic nucleic acid" that functions in a cell or under physiological conditions as a naturally occurring miRNA.

While many of the embodiments of the invention involve synthetic miRNAs or synthetic nucleic acids, in some embodiments of the invention, the nucleic acid molecule(s) need not be "synthetic." In certain embodiments, a non-synthetic miRNA employed in methods and compositions of the invention may have the entire sequence and structure of a naturally occurring miRNA precursor or the mature miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not an miRNA that qualifies as "synthetic"); though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

In other embodiments of the invention, there are synthetic nucleic acids that are miRNA inhibitors. An miRNA inhibitor is between about 17 to 25 nucleotides in length and comprises a 5' to 3' sequence that is at least 90% complementary to the 5' to 3' sequence of a mature miRNA. In certain embodiments, an miRNA inhibitor molecule is 17, 18, 19, 20, 21, 22, 23, 24, or 25 nucleotides in length, or any range derivable therein. Moreover, an miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. Probe sequences for miRNAs are disclosed in the appendix. While they have more sequence than an miRNA inhibitor, one of skill in the art could use that portion of the probe sequence that is complementary to the sequence of a mature miRNA as the sequence for an miRNA inhibitor. Table 1 indicates what the mature sequence of an miRNA is. Moreover, that portion of the probe sequence can be altered so that it is still 90% complementary to the sequence of a mature miRNA.

In some embodiments, of the invention, a synthetic miRNA contains one or more design elements. These design elements include, but are not limited to: i) a replacement group for the phosphate or hydroxyl of the nucleotide at the 5' terminus of the complementary region; ii) one or more sugar modifications in the first or last 1 to 6 residues of the complementary region; or, iii) noncomplementarity between one or more nucleotides in the last 1 to 5 residues at the 3' end of the complementary region and the corresponding nucleotides of the miRNA region.

miRNAs are apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with an miRNA sequence having at least one of the three designs is referred to as a synthetic miRNA.

Synthetic miRNAs of the invention comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, called the synthetic miRNA, that is similar to the naturally occurring miRNA precursor that is bound by the protein complex immediately prior to miRNA activation in the cell. Maximizing activity of the synthetic miRNA requires maximizing uptake of the active strand and minimizing uptake of the complementary strand by the miRNA protein complex that regulates gene expression at the level of translation. The molecular designs that provide optimal miRNA activity involve modifications to the complementary strand.

Two designs incorporate chemical modifications in the complementary strand. The first modification involves creating a complementary RNA with a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including $NH_2$, $NHCOCH_3$, biotin, and others.

The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance synthetic miRNA activities.

The third synthetic miRNA design involves incorporating nucleotides in the 3' end of the complementary strand that are not complementary to the active strand. Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of the synthetic miRNA.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluoroscein, a thiol, or acridine, though other replacement groups are well known to those of skill in the art and can be used as well. This design element can also be used with an miRNA inhibitor.

Additional embodiments concern a synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there is one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification. In further embodiments, there is one or more sugar modifications in the first or last 2 to 4 residues of the complementary region or the first or last 4 to 6 residues of the complementary region. This design element can also be used with an miRNA inhibitor. Thus, an miRNA inhibitor can have this design element and/or a replacement group on the nucleotide at the 5' terminus, as discussed above.

In other embodiments of the invention, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is noncomplementarity with at least 2 nucleotides in the complementary region.

It is contemplated that synthetic miRNA of the invention have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

The invention also provides peptide inhibitors. For example, the invention provides peptides inhibitors of cathepsin G, such as, Z-gly-leu-phe-chloromethyl ketone (Enzyme Systems Products Livermore, Calif.), cathepsin G inhibitor 1 ($C_{36}H_{33}N_2O_6P$) (EMD Chemicals Inc, Darmstadt, Germany), Gly-Leu-Phe, benzyloxycarbonyl-Gly-Leu-Phe-chloromethyl ketone, Ala-Ala-Pro-Phe (SEQ ID NO: 9), N-(Methoxysuccinyl)-Ala-Ala-Pro-Phe-chloromethyl ketone (SEQ ID NO: 10), Ala-Ala-Pro-Val (SEQ ID NO: 11), N-(Methoxysuccinyl)-Ala-Ala-Pro-Val-chloromethyl ketone (SEQ ID NO: 12), Acetyl-Thr-Glu-Phe-Gly-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-Tyr-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-Gly-OH (acetyl-eglin C) (SEQ ID NO: 13), Pro-Val-Thr-Leu (SEQ ID NO: 14), Ser-Pro-Val-Thr-Leu-Asp-Leu-Arg-Tyr (SEQ ID NO: 15), monocyte neutrophil elastase inhibitor, maspin, secretory leukocyte protease inhibitor, Gly-Thr-Glu-Ala-Ala-Ala-Ala-Thr-Ala-Gly-Ile-Ala-Thr-Phe-Cys (SEQ ID NO: 16), Met-Leu-Met-Phe-Glu-Glu-Asn-Phe-Thr-Ala-Asp-His-Pro-Phe (SEQ ID NO: 17), Gly-Thr-Glu-Ala-Ala-Ala-Ala-Thr-Gly-Gly-Ile-Ala-Thr-Phe-Cys (SEQ ID NO: 18), Met-Leu-Leu-Pro-Glu-Glu-Glu-Phe-Thr-Val-Asp-His-Pro-Phe (SEQ ID NO: 19), Gly-Thr-Glu-Ala-Ala-Ala-Ala-Thr-Gly-Gly-Ile-Ile-Gln-Val-Leu-Cys-Glu-Lys-Met-Pro-Thr-Pro-Gln-Glu-Val-Phe-Thr-Val-Asp-His-Pro-Phe (SEQ ID NO: 20), —ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3, or Ac-Ala-Ala-ANle-OEt.

The methods of the invention can also use STAT1 inhibitors such as STAT1beta (SignalChem, British Columbia, CA).

The invention also provides small molecule inhibitors of the identified targets. For example, the methods of the invention can use the IL-6 inhibitors Am-80 (Innovive Pharmaceuticals, NY, N.Y.), Madindolines A and B (natural products isolated from Streptomyces), 20S,21-Epoxy-resibufogenin-3-formate (natural product isolated from bufadienolide). In other embodiments, the invention also provides STAT1 inhibitors, for example, parthenolide (Fermentek Ltd., Jerusalem, Ill.).

The invention further provides methods (also referred to herein as a "screening assay") for identifying or testing modulators, i.e., candidate or test compounds or agents (e.g., peptides, peptidomimetics, nucleic acids, siRNAs, shRNAs, microRNAs, small molecules, or other drugs) that bind to the molecules identified herein, e.g., IL6, INFγ, cathepsin G, or STAT1 proteins or nucleic acids, or have an inhibitory effect on, for example, the expression or activity of these molecules.

The test compounds, also referred to herein as "candidate inhibitor" of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869), or phage (Scott and Smith (1990) Science 249:386-390; Devlin (1990) Science 249:404-406; Cwirla et al. (1990) Proc. Natl. Acad. Sci. USA 87:6378-6382; and Felici (1991) J. Mol. Biol. 222:301-310).

Determining the ability of the test compound to bind and or inhibit the activity or expression of, for example, IL6, INFγ, cathepsin G, or STAT1 can be accomplished by a variety of methods. In one embodiment, the test compounds can be assayed for the ability to inhibit Nrf to using luciferase transfected cancer cells as described in the examples. Additionally, the assay could be conducted by coupling the test compound with a radioisotope or enzymatic label such that binding of the test compound to the protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In one embodiment, the assay components described herein can be packaged into a kit along with instructions for use. For example, the luciferase transfected cancer cells can be included in a kit comprising instructions for determining if a candidate compound is an inhibitor of the expression or activity of, for example, IL6, INFγ, cathepsin G, or STAT1.

In a similar manner, one may determine the ability of a protein to bind to or interact with a target molecule. By "target molecule" is intended a molecule with which a IL6, INFγ, cathepsin G, or STAT1 protein binds or interacts in nature. In a preferred embodiment, the ability of a protein to bind to or interact with a target molecule can be determined by monitoring the activity of the target molecule. Also for example, the activity of the target molecule can be monitored by detecting induction of a cellular second messenger of the target, detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, cellular differentiation or cell proliferation.

In yet another embodiment, an assay of the present invention is a cell-free assay comprising contacting a protein or biologically active portion thereof with a test compound and determining the ability of the test compound to bind to the protein or biologically active portion thereof. Binding of the test compound to the protein, e.g., IL6, INFγ, cathepsin G, or STAT1, can be determined either directly or indirectly as described above. In a preferred embodiment, the assay includes contacting the protein or biologically active portion thereof with a known compound that binds the protein to form an assay mixture, contacting the assay mixture with a test compound, and determining the ability of the test compound to preferentially bind to the target protein or biologically active portion thereof as compared to the known compound.

In another embodiment, an assay is a cell-free assay comprising contacting a protein or biologically active portion thereof with a test compound and determining the ability of the test compound to modulate (e.g., stimulate or inhibit) the activity of the protein or biologically active portion thereof. Determining the ability of the test compound to modulate the activity of a protein can be accomplished, for example, by determining the ability of the protein to bind to a target molecule as described above for determining direct binding. In an alternative embodiment, determining the ability of the test compound to modulate the activity of a protein can be accomplished by determining the ability of the protein to further modulate a target molecule. For example, the catalytic/enzymatic activity of the target molecule on an appropriate substrate can be determined as previously described.

In yet another embodiment, the cell-free assay comprises contacting the protein, e.g., IL6, INFγ, cathepsin G, or STAT1 or biologically active portion thereof with a known compound that binds the protein to form an assay mixture, contacting the assay mixture with a test compound, and determining the ability of the test compound to preferentially bind to or modulate the activity of a target molecule.

In the above-mentioned assays, it may be desirable to immobilize either the protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or the protein of interest, e.g., IL6, INFγ, cathepsin G, or STAT1, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either a protein or its target molecule can be immobilized utilizing conjugation of biotin and streptavidin. Biotinylated molecules or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a protein or target molecules but which do not interfere with binding of the protein to its target molecule can be derivatized to the wells of the plate, and unbound target or the protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays that rely on detecting an enzymatic activity associated with the protein or target molecule.

In another embodiment, modulators of expression of, for example, IL6, INFγ, cathepsin G, or STAT1, are identified in a method in which a cell is contacted with a candidate compound and the expression of mRNA or protein in the cell is determined relative to expression of mRNA or protein in a cell in the absence of the candidate compound. When expression is greater (statistically significantly greater) in the presence of the candidate compound than in its absence, the candidate compound is identified as a stimulator of mRNA or protein expression. Alternatively, when expression is less (statistically significantly less) in the presence of the candidate compound than in its absence, the candidate compound is identified as an inhibitor of mRNA or protein expression. The level of mRNA or protein expression in the cells can be determined by methods described herein for detecting mRNA or protein.

In yet another aspect of the invention, the proteins identified herein, e.g., IL6, INFγ, cathepsin G, or STAT1, can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300), to identify other proteins, which bind to or interact with the identified protein and modulate protein activity. Such binding proteins are also likely to be involved in the propagation of signals by the proteins as, for example, upstream or downstream elements of the pathway.

This invention further pertains to novel agents identified by the above-described screening assays and uses thereof for treatments as described herein.

Pharmaceutical Compositions

The methods of the invention comprises administration of one or more compounds to a subject. In particular embodiments, the compound is a pharmaceutical composition, a therapeutic agent or small molecule, a nucleic acid molecule, a monoclonal, polyclonal, chimeric or humanized antibody.

Pharmaceutical compositions encompassed by the present invention include as active agents, the peptides, polypeptides, polynucleotides, siRNA, shRNA, miRNA, antisense oligonucleotides, small molecules, or antibodies of the invention disclosed herein in a therapeutically effective amount. An "effective amount" is an amount sufficient to effect beneficial or desired results, including clinical results. An effective amount can be administered in one or more administrations. For purposes of this invention, an effective amount is an amount that is sufficient to palliate, ameliorate, stabilize, reverse, slow or delay the progression of the disease state.

The compositions can be used to treat any one of the numerous conditions disclosed herein. In addition, the pharmaceutical compositions can be used in conjunction with conventional additional methods of treatment, e.g., to increase the efficacy of either treatment alone. The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

A "patient" or "subject" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg of the compositions of the present invention in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The pharmaceutical compositions of the present invention can comprise a compound in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1-100% wgt/vol. Once formulated, the compositions contemplated by the invention can be (1) administered directly to the subject (e.g., as polynucleotide, polypeptides, small molecule agonists or antagonists, and the like); or (2) delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Targeted delivery of therapeutic compositions containing an antisense polynucleotide, subgenomic polynucleotides, or antibodies to specific tissues can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1.mu.g to about 2 mg, about 5.mu.g to about 500.mu.g, and about 20.mu.g to about 100.mu.g of DNA can also be used during a gene therapy protocol. Factors such as method of action (e.g., for enhancing or inhibiting levels of the encoded gene product) and efficacy of transformation and expression are considerations that will affect the dosage required for ultimate efficacy of the antisense subgenomic polynucleotides. Where greater expression is desired over a larger area of tissue, larger amounts of antisense subgenomic polynucleotides or the same amounts re-administered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, Mol. Cell. Biol. (1994) 14:2411, and in Woffendin, Proc. Natl. Acad. Sci. (1994) 91:1581.

Further non-viral delivery suitable for use includes mechanical delivery systems such as the approach described in Woffendin et al., Proc. Natl. Acad. Sci. USA (1994) 91(24):11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

The administration of the inhibitors of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly.

In a preferred embodiment, the inhibitors are administered as therapeutic agents, and can be formulated as outlined above. Similarly, genes (including both the full-length sequence, partial sequences, or regulatory sequences of the coding regions) and other nucleic acid sequences can be administered in gene therapy applications, as is known in the art. These genes can include antisense applications, either as gene therapy (i.e. for incorporation into the genome) or as antisense compositions, as will be appreciated by those in the art.

Methods of the Invention

The instant invention provides methods of inhibiting platelet aggregation or clot formation in a subject, and methods of treating diseases and disorders characterized by platelet aggregation or clot formation. Specifically, in one embodiment, the invention provides methods of inhibiting platelet aggregation or clot formation by decreasing the amount of neutrophils. As taught herein, the amount or activity of neutrophils can be modulated by inhibiting the production or activity of cathepsin G, IL6, INFγ, or STAT1. The invention also provides methods for treating diseases and disorders characterized by platelet aggregation or clot formation by modulating the activity or expression of cathepsin G inhibiting the production or activity of IL6, INFγ, or STAT1.

The instant invention provides methods for the treatment or prevention of vascular occlusive disease, ischemia/reperfusion injury, acute or chronic inflammatory states, autoimmune diseases, myelodysplastic syndromes, tissue injury from surgery or accidental traumas, acute bacterial or viral infections, undergone a microvascular surgical reconstructive procedures, patients receiving granulocyte colony stimulating factor therapy, patients receiving stem cell therapy, or patients having sickle cell anemia.

Specifically, in one embodiment, the invention provides methods of treating subjects having acute or chronic inflammatory state as defined by: peripheral blood total leukocyte count $>7\times10^3/\mu l$; peripheral blood neutrophil count $>4\times10^3/\mu l$; or, plasma IL-6 concentration $>3$ pg/ml.

In another embodiment, the invention provides methods of treating or preventing autoimmune diseases, e.g., Rheumatoid Arthritis, Systemic Lupus Erythematosis, Sjogren's Disease, or Scleroderma.

In another embodiment, the invention provides methods of treating or preventing myelodysplastic syndromes, e.g., acute myelogenous leukemia, or chronic myelogenous leukemia.

As used herein, "myelodysplastic syndrome" is intended to refer to a diverse collection of hematological conditions united by ineffective production of blood cells and varying risks of transformation to acute myelogenous leukemia (AML). Myelodysplastic syndromes (MDS) are bone marrow stem cell disorders resulting in disorderly and ineffective hematopoiesis (blood production) manifested by irreversible quantitative and qualitative defects in hematopoietic (blood-forming) cells. Exemplary myelodysplastic syndromes include acute myelogenous leukemia and chronic myelogenous leukemia.

In another embodiment, the invention provides methods of treating tissue injury from surgery or accidental trauma.

In another embodiment, the invention provides methods of treating or preventing acute bacterial or viral infection, e.g., pneumonia, bronchitis, urinary tract infection, or sepsis.

In another embodiment, the invention provides methods of treating a subject recovering from a microvascular surgical reconstructive procedure.

In another embodiment, the invention provides methods of treating a subject receiving granulocyte colony stimulating factor therapy, e.g., before or after bone marrow transplant, or for mobilization of peripheral stem cells.

In another embodiment, the invention provides methods of treating or preventing vascular occlusive diseases, e.g., heart attack, myocardial infarction, unstable angina, stroke, peripheral arterial occlusive disease, thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

In another embodiment, the invention provides methods of treating or preventing ischemia or a reperfusion injury, e.g., due to administration of fibrinolytic therapy to an occluded cerebral, coronary, or peripheral artery; balloon angioplasty or arterecteomy/atherectomy of a cerebral, coronary, or peripheral artery; or, clamping of the aorta or major organ vessel during surgery As used herein, "vascular occlusive disease" refers to a number of diseases and disorders characterized by histological narrowing and occlusion of veins and arteries. Exemplary vascular occlusive diseases are disclosed herein.

The term "platelet aggregation" as used herein refers to the clumping together of platelets in the blood. Platelet aggregation is part of the sequence of events leading to the formation of a clot, or thrombus, formation and can be detrimental to the health of an individual.

Thus, in one embodiment, methods of modulating gene activity in cells or organisms are provided. In one embodiment, the methods comprise administering to a cell an antibody that reduces or eliminates the biological activity of an endogenous protein, e.g., cathepsin G, IL6, INFγ, or STAT1. As will be appreciated by those in the art, this may be accomplished in any number of ways.

The instant invention also provides methods and compositions for preventing or treating a subject that has or is at risk of developing platelet aggregation or clot formation that has become resistant to standard aspirin therapy.

As used herein, "aspirin resistance" is intended to mean a condition wherein a subject does not respond to aspirin for treating or preventing platelet aggregation, as commonly used to reduce the risk of vascular occlusion. Aspirin therapy is known to be an effective method of preventing heart attacks and strokes by irreversibly inhibiting platelet aggregation. However, some population of patients develop a resistance to this treatment.

The term "therapeutically effective amount" is intended to include an amount of a compound useful in the present invention or an amount of the combination of compounds claimed, e.g., to treat or prevent the disease or disorder, or to treat the symptoms of the disease or disorder, in a subject.

In one embodiment, the subject is administered a combination of compounds. The combination could be two or more compounds described herein, or one or more compound described herein and one or more compounds that are know in the art for treatment of the particular disease or disorder which the subject has or is at risk of developing. In one embodiment, the combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components. According to the present invention a combination treatment is defined as affording a synergistic effect if the effect is therapeutically superior, as measured by, for example, the extent of the response, the response rate, the time to disease progression or the survival period, to that achievable on dosing one or other of the components of the combination treatment at its conventional dose. For example, the effect of the combination treatment is synergistic if the effect is therapeutically superior to the effect achievable with either compound or treatment alone. Further, the effect of the combination treatment is synergistic if a beneficial effect is obtained in a group of patients that does not respond (or responds poorly) to a particular treatment alone. In addition, the effect of the combination treatment is defined as affording a synergistic effect if one of the components is dosed at its conventional dose and the other component(s) is/are dosed at a reduced dose and the therapeutic effect, as measured by, for example, the extent of the response, the response rate, the time to disease progression or the survival period, is equivalent to that achievable on dosing conventional amounts of the components of the combination treatment.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition According to the present invention, methods of treatment in individuals who have been identified as having, or at risk of developing a particular disease, disorder of condition are performed by delivering to such individuals an amount of a compound, e.g., an inhibitor of cathepsin G, IL6, INFγ, or STAT1 activity or expression, sufficient to induce the desired clinical outcome.

The pharmaceutical compositions described above may be administered by any means that enables the active agent to reach the agent's site of action in the body of the individual. The dosage administered varies depending upon factors such as: pharmacodynamic characteristics; its mode and route of administration; age, health, and weight of the recipient; nature and extent of symptoms; kind of concurrent treatment; and frequency of treatment.

The amount of compound administered will be dependent on the subject being treated, on the subject's weight, the severity of the affliction, the manner of administration and the judgment of the prescribing physician. In some embodiments, the dosage range would be from about 1 to 3000 mg, in particular about 10 to 1000 mg or about 25 to 500 mg, of active ingredient, in some embodiments 1 to 4 times per day, for an average (70 kg) human. Generally, activity of individual compounds used in the invention will vary.

Dosage amount and interval may be adjusted individually to provide plasma levels of the compounds which are sufficient to maintain therapeutic effect. Usually, a dosage of the active ingredient can be about 1 microgram to 100 milligrams per kilogram of body weight. In some embodiments a dosage is 0.05 mg to about 200 mg per kilogram of body weight. In another embodiment, the effective dose is a dose sufficient to deliver from about 0.5 mg to about 50 mg. Ordinarily 0.01 to 50 milligrams, and in some embodiments 0.1 to 20 milligrams per kilogram per day given in divided doses 1 to 6 times a day or in sustained release form is effective to obtain desired results. In some embodiments, patient dosages for administration by injection range from about 0.1 to 5 mg/kg/day, preferably from about 0.5 to 1 mg/kg/day. Therapeutically effective serum levels may be achieved by administering multiple doses each day. Treatment for extended periods of time will be recognized to be necessary for effective treatment.

In some embodiments, the route may be by oral administration or by intravenous infusion. Oral doses generally range from about 0.05 to 100 mg/kg, daily. Some compounds used in the invention may be orally dosed in the range of about 0.05 to about 50 mg/kg daily, while others may be dosed at 0.05 to about 20 mg/kg daily.

The invention also provides kits for the treatment of disease comprising one or more of the compounds described herein and instructions for use.

Diagnostic Methods

The present invention encompasses methods for diagnosing the presence of a vascular occlusive disease, and for the identification of subjects with an increased likelihood of developing such conditions. In certain embodiments, the methods pertain to measuring the amount of activity of cathepsin G, IL6, or interferon-gamma in serum, plasma, or leukocytes.

An exemplary method for detecting the presence or absence of cathepsin G, IL6, or interferon-gamma proteins or nucleic acid in a biological sample involves obtaining a biological sample from a test subject and contacting the biological sample with a compound or an agent capable of detecting cathepsin G, IL6, or interferon-gamma proteins or nucleic acid (e.g., mRNA, or genomic DNA) that encodes cathepsin G, IL6, or interferon-gamma protein such that the presence of the protein or nucleic acid is detected in the biological sample. A preferred agent for detecting mRNA or genomic DNA is a labeled nucleic acid probe capable of hybridizing to mRNA or genomic DNA. The nucleic acid probe can be, for example, the an oligonucleotide of at least 15, 20, 25, 30, 35, 40, 45, 50, 100, 250 or 500 nucleotides in length and sufficient to specifically hybridize under stringent conditions to mRNA or genomic DNA. Other suitable probes for use in the diagnostic assays of the invention are described herein and can be determined by those of skill in the art.

A preferred agent for detecting cathepsin G, IL6, or interferon-gamma proteins is an antibody capable of binding to one of these proteins, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect cathepsin G, IL6, or interferon-gamma mRNA, protein, or genomic DNA in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting cathepsin G, IL6, or interferon-gamma proteins, mRNA, or genomic DNA, such that the presence of the protein, mRNA or genomic DNA is detected in the biological sample, and comparing the presence of cathepsin G, IL6, or interferon-gamma protein, mRNA or genomic DNA in the control sample with the presence of the protein, mRNA or genomic DNA in the test sample.

The invention also encompasses kits for detecting the presence of cathepsin G, IL6, or interferon-gamma in a biological sample. For example, the kit can comprise a labeled compound or agent capable of detecting cathepsin G, IL6, or interferon-gamma protein or mRNA in a biological sample; means for determining the amount of cathepsin G, IL6, or interferon-gamma in the sample; and means for comparing the amount of in the sample with a standard. The compound or agent can be packaged in a suitable container. The kit can further comprise instructions for using the kit to detect cathepsin G, IL6, or interferon-gamma protein or nucleic acid.

Using the above identified methods, a clinician can determine the presence of, or the likelihood of a subject developing, a disease, disorder or condition, e.g., a vascular occlusive disease. In exemplary embodiments, an increase in the presence or activity of cathepsin G, IL6, or interferon-gamma protein or nucleic acid is indicative of the presence of, or the likelihood of a subject developing, a disease, disorder or condition, e.g., a vascular occlusive disease.

EXAMPLES

It should be appreciated that the invention should not be construed to be limited to the examples that are now described; rather, the invention should be construed to include any and all applications provided herein and all equivalent variations within the skill of the ordinary artisan.

The data presented in the following examples identify inhibitors of cathepsin G (e.g. $C_{36}H_{33}N_2O_6P$, Z-Gly-Leu-Phe-CMK) as a novel class of anti-thrombotic compounds that is specifically indicated for use under conditions of systemic inflammation as defined by: 1) acute infection, trauma (surgical or accidental) or vaccination, or 2) in the presence of chronically or acutely elevated blood leukocyte count (e.g. total leukocyte count $>\sim 7\times 10^3/\mu l$, or neutrophil count $>\sim 4\times 10^3/\mu l$) or increased levels of IL-6 (plasma concentration $>\sim 3$ pg/ml). The data also identify cathepsin G inhibitors as a novel class of compounds that are specifically indicated as an alternative or in addition to aspirin when resistance/failure of aspirin treatment has already occurred (e.g. treatment after MI/stroke that has occurred despite aspirin treatment) or is likely to occur (e.g. prophylaxis against MI/stroke after infection). The data also demonstrate, among other applications, a novel uses for the cathepsin G class of antithrombtic agents for the prevention or treatment of primary and secondary prevention of MI, stroke, or peripheral arterial occlusion after bacterial or viral infection or vaccination (e.g. after pneumonia, bronchitis, urinary tract infection, sepsis, clinical influenza or vaccination against viral illnesses, etc.); primary and secondary prevention of MI, stroke, or peripheral arterial occlusion after accidental injury or surgical trauma; prevention of arterial, venous, or synthetic conduit occlusion after surgical coronary, carotid, or peripheral revascularization procedure; maintenance of vascular patency after surgical reconstructive flap procedure; primary and secondary prevention of MI, stroke, and peripheral arterial occlusion in patients with chronically or acutely elevated leukocyte counts; primary and secondary prevention of MI, stroke, and peripheral arterial occlusion in patients with chronic autoimmune states such as rheumatoid arthritis and systemic lupus erythematosis; primary and secondary prevention of MI and stroke in patients with sickle cell anemia; secondary prevention of MI, stroke, and peripheral arterial occlusion in patients who have suffered an atherothrombotic event despite aspirin treatment; prevention of postoperative deep venous thrombosis; prevention of arterial and venous thrombosis in patients with chronic and acute myelogenous leukemia; prevention of arterial and venous thrombosis in patients treated with GCSF following bone marrow transplant; prevention of arterial and venous thrombosis in patients treated with GCSF for stem cell mobilization; prevention of arterial and venous thrombosis in patients treated with stem cells.

Example 1

Neutrophils Enhance Platelet Aggregation In Vitro

Figure 1:
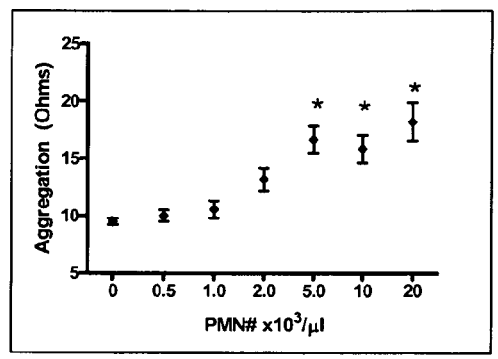
FIG. 1 demonstrates that neutrophils enhance platelet aggregation in vitro. Human neutrophils (PMN) were isolated by his opaque centrifugation and cultured in RPMI/5% human serum for 24 hours. Neutrophils were reconstituted with freshly prepared platelet rich plasma, and impedance aggregometry (in response to 15 μM TRAP) was assessed in the absence (0) or presence of increasing concentrations of PMNs. N=8, means significantly different by one way ANOVA (P<0.0001), *P<0.05 vs. 0, 0.5, and 1.0 by Bonferroni corrected post-hoc test.

Neutrophils comprise 40-75% of the circulating leukocyte population in humans but this range is dramatically widened under pathologic conditions. Because neutrophil counts vary dramatically in humans under normal and proinflammatory conditions, we assessed the dose-response relationship between neutrophil number and platelet aggregation ex vivo. For these experiments, neutrophils were isolated from heparin-anticoagulated whole blood by histopaque centrifugation (>95% neutrophil subtype) and cultured in RPMI/5% autologous serum for 24 hours. Neutrophils were reconstituted with freshly prepared platelet rich plasma (PRP) from the same donor who provided blood for neutrophil isolation 24 hours earlier. Escalating numbers of neutrophils were combined with platelets through a physiologic to pathologic range, and impedance aggregometry in response to thrombin receptor activating peptide (TRAP) and collagen were assessed. Results for these experiments are shown in FIG. 1 and demonstrate a clear dose-response relationship between neutrophil number and platelet aggregation that is evident throughout a clinically encountered physiologic ($2\times10^3$/µl) to pathologic range ($20\times10^3$/µl). Similar results were observed when collagen was used as the agonist (data not shown).

Example 2

Figure 2:
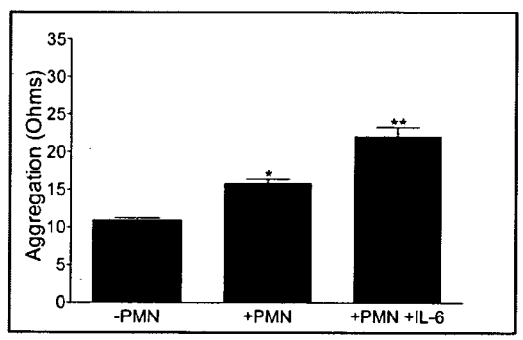
FIG. 2 depicts IL-6-treated neutrophils augment platelet aggregation in vitro. Human neutrophils (PMN) were isolated by histopaque centrifugation and cultured in RPMI/5% human serum for 24 hours in the presence of IL-6 (10 ng/ml) or vehicle. Platelet rich plasma was freshly prepared from the same donor, and impedance aggregometry (in response to 15 μM TRAP) was performed in the absence (—PMN) or presence of untreated PMN (+PMN), or IL-6-treated PMN (+PMN+IL-6). N=8, *P<0.01 vs. –PMN, **P<0.01 vs. –PMN and +PMN FIG. 3 demonstrates that lymphocytes do not enhance platelet aggregation in vitro. Human lymphocytes (LYMPH) were isolated by negative magnetic bead separation and cultured in RPMI/5% human serum for 24 hours in the presence of IL-6 (10 ng/ml) or vehicle. Platelet rich plasma was freshly prepared from the same donor, and impedance aggregometry (in response to 15 μM TRAP) was performed in the absence (–LYMPH) or presence of untreated LYMPH (+LYMPH) or IL-6-treated LYMPH (+LYMPH+IL-6). N=8

IL-6 Augments the Ability of Neutrophils to Enhance Platelet Aggregation in Vitro Experiments demonstrated that physiologic numbers of neutrophils exerted a moderate effect on platelets by enhancing aggregation by 25-50%[19]. We tested whether this effect would increase under the pro-inflammatory influence of IL-6. IL-6 is a candidate inflammatory cytokine that could link systemic inflammation to atherothrombotic disorders. IL-6 is widely expressed in human tissues in response to infection, tissue trauma, or immunologic challenge[20], and plasma levels are associated with future risk of MI and cardiovascular death in asymptomatic individuals and patients with CAD[10, 11]; however, its ability to modulate the effect of neutrophils on platelets or thrombus formation had not been assessed. To test the hypothesis, human neutrophils were isolated by histopaque centrifugation and incubated cells in the presence of IL-6 (10 ng/ml) or vehicle for 24 hours. Neutrophils were reconstituted with freshly isolated PRP at a final concentration of $2\times10^3$ neutrophils/µl and $170\times10^3$ platelets/µl (a neutrophil-platelet ratio encountered under normal physiologic conditions). IL-6-treated neutrophils increased TRAP-induced aggregation compared to PRP alone or PRP in the presence of vehicle-treated neutrophils, doubling aggregation over what was observed in PRP alone (FIG. 2). Similar results were seen when collagen was used to stimulate platelet aggregation instead of TRAP.

Figure 3:
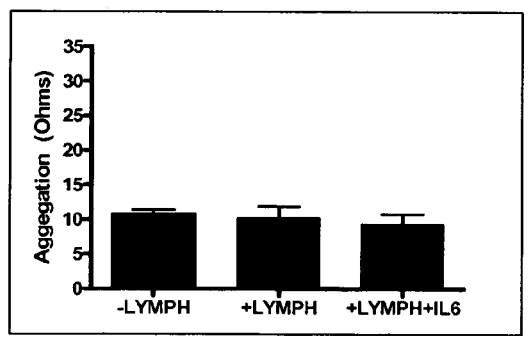

To gain perspective on the specificity of leukocyte subtype for enhancement of platelet activation, the effect of lymphocytes on platelet aggregation was examined in vitro. Lymphocytes were isolated from heparin-anticoagulated whole blood by negative magnetic-antibody isolation (Dynal, purity >95%) and cultured in the presence and absence of IL-6 (10 ng/ml) for 24 hours. Similar to the neutrophil protocol, lymphocytes were reconstituted with freshly prepared PRP ($2\times10^3$ lymphocytes/µl and $170\times10^3$ platelets/µl) and impedance aggregation in response to thrombin receptor activating peptide (TRAP) and collagen were assessed. In contrast to neutrophils, the presence of lymphocytes did not increase platelet aggregation in response to TRAP (FIG. 3) and IL-6 pre-treatment had no significant effect on aggregation. In the presence of lymphocytes, diminished platelet aggregation in response to collagen was observed and IL-6 had no impact.

Example 3

Neutrophils Participate in Hemostasis In Vivo

Figure 4:
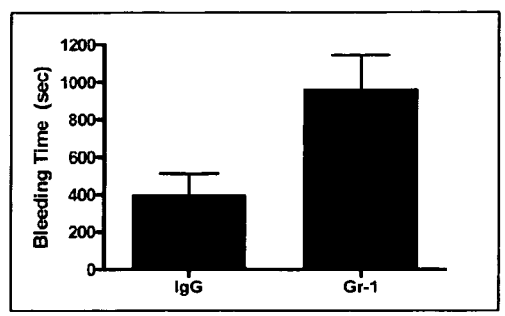
FIG. 4 depicts neutrophil depletion prolongs bleeding time in vivo in the mouse. Mice were injected intraperitoneally with neutrophil depleting antibody (Gr-1, 0.25 mg) or isotype control (IgG). Two days later, bleeding times were assessed in anesthetized mice after amputating the distal 3 mm section of tail. Time to visual cessation of bleeding was recorded. N=3 control and 4 antibody-treated, P=0.06.

In vitro experiments indicated that neutrophils could modify platelet function in vitro. To determine if neutrophils participated in hemostasis in vivo standardized bleeding time in mice was examined after manipulating the number of circulating neutrophils. Briefly, C57BL6/J wild-type mice were injected intraperitoneally with anti-neutrophil antibody (Gr-1, 0.25 mg) or isotype control. Two days later mice were anesthetized with ketamine (80 mg/kg)/xylazine (13 mg/kg) and tail bleeding was performed by amputating a 3 mm section of the distal tail and immersing it in 37° C. PBS. The time to visual cessation of bleeding was recorded. At the end of each experiment, blood was obtained by retro-orbital puncture and complete blood counts determined by automated cell counter (HemaVet). Gr-1 antibody reduced neutrophil counts by ~80% compared to IgG control animals ($0.44\pm0.24$ vs. $0.08\pm0.03\times10^3$/µl, N=7), although this difference did not reach statistical significance given the limited number of experiments. There was no difference in the number of monocytes (0.06±0.01 vs. 0.05±0.01×10$^3$/μl) and a moderate reduction in the number of lymphocytes (2.24±0.16 vs. 1.40±0.21×10$^3$/μl) with Gr-1 antibody treatment. Results from bleeding time experiments are shown in FIG. 4 and demonstrate prolonged bleeding times in neutrophil depleted animals.

Example 4

Figure 5:
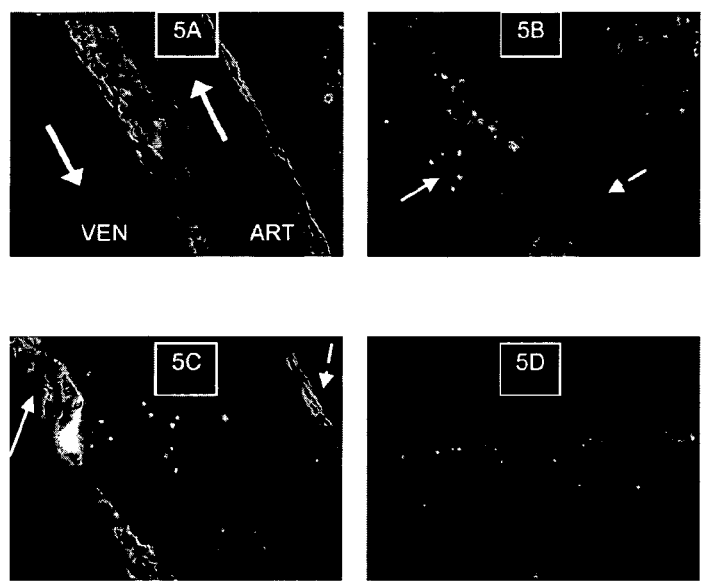
FIGS. 5A-D depict incorporation of leukocytes into microvascular thrombi. A. Baseline prior to ferric chloride injury. VEN=venule, ART=arteriole, arrows indicate direction of blood flow. B. 1 minute after ferric chloride injury. Arrows indicate rolling of leukocytes in venule and arteriole. C. 10 minutes after ferric chloride injury. Arrows indicate incorporation of leukocyte-related fluorescence into developing thrombi in venule and arteriole. D. Dual fluorescent image of rhodamine-labeled leukocytes (red) and calcein-labeled platelets (green) co-localizing into developing thrombus.
Figure 6:
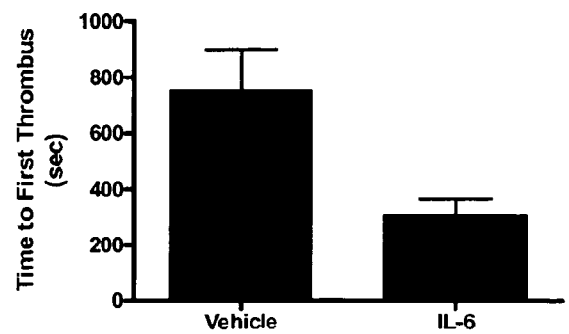
FIG. 6 demonstrates that IL-6 accelerates thrombus formation in vivo. Mice were treated with IL-6 (2×100 ng/100 μl IM injection) or vehicle for 48 hours. Microvascular injury was induced with ferric chloride and time to arteriolar thrombus formation >10 μm determined from digital images. *P=0.02, N=8 vehicle, N=6 IL-6-treated.

IL-6 Accelerates In Vivo Thrombus Formation in a Mouse Microvascular Injury Model In vitro experiments indicated that IL-6 enhanced the ability of neutrophils to augment platelet aggregation. We sought to determine the in vivo effect of exogenous IL-6 on thrombus formation. Microvascular thrombus formation was assessed using intravital fluorescence microscopy as previously described[21] with modification. Briefly, C57BL6/J mice were treated with IL-6 (100 ng/100 μl) or vehicle by intramuscular injection on two consecutive days. Two days after the first injection, mice were anesthetized with ketamine/xylazine and injected intravenously with rhodamine-6-G (50 μl of 0.05% solution) to label circulating leukocytes[22]. Mesentery was exteriorized through a midline abdominal incision, and arterioles (60-80 μm) and venules (120-150 μm) were visualized using an inverted fluorescence microscope (Nikon). Endothelial damage was induced by topical application of ferric chloride (250 or 500 μM) and images of leukocyte adherence to damaged endothelium and incorporation into thrombi were recorded with a digital camera (Retiga). Time to formation of first thrombus, defined as a thrombus >10 μm in diameter, was determined from digital images. In some experiments, we performed dual labeling of leukocytes and platelets. For these experiments, platelets were isolated from peripheral blood of control mice, labeled in vitro with calcein-AM (1 μM for 20 min), and injected intravenously (1×10$^8$ platelets) prior to rhodamine injection. FIG. 5 shows images from control experiments indicating adherence of rhodamine-treated leukocytes to ferric chloride-injured microvasculature and their incorporation into growing thrombi. FIG. 6 demonstrates that IL-6-treatment shortens the time to formation of first thrombus by greater than 50%.

Example 5

Neutrophils Release Cathepsin G in the Presence of Activated Platelets-Modulation by IL-6

Cathepsin G is a serine protease and strong platelet activator that is released from neutrophil azurophilic granules after cell activation[23-25]. Release of platelet activators from neutrophils requires neutrophil activation, which can be induced by engagement of neutrophil receptors for bacterial products[23] (e.g. formyl-methionine-leucine-phenylalanine [f-MLP]), cytokines[24] (e.g. tumor necrosis factor [TNF]), or adhesion molecules[26, 27] (e.g. P-selectin glycoprotein ligand-1 [PSGL-1]). Neutrophil binding to P-selectin on activated platelets appears to be a sufficient stimulus to activate neutrophil kinases[26, 27] and to release granule proteases[28]; however, the release of cathepsin G from neutrophils in the presence of activated platelets had not been investigated.

Figure 7A:
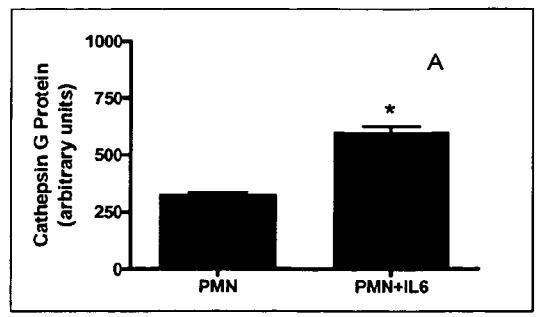
FIG. 7A demonstrates that neutrophil expression of cathepsin G increases in the presence of IL-6. Human neutrophils (PMN) were cultured in the absence and presence of IL-6 (10 ng/ml) for 24 hours. Cells were harvested, lysed, and cathepsin G protein identified by Western blotting (10 μg/lane). Proteins were visualized by enhanced chemiluminescence and quantified by densitometry. *P<0.01
Figure 7:
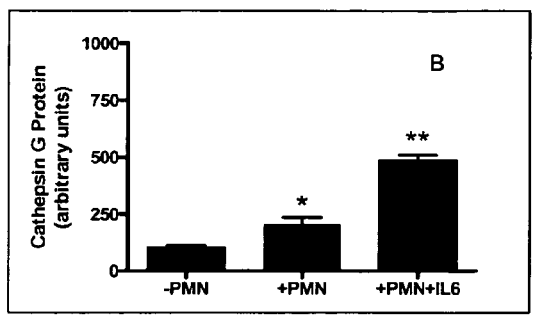
FIG. 7B demonstrates that neutrophil secretion of cathepsin G increases in the presence of activated platelets and pre-treatment with IL-6. Platelet rich plasma (—PMN) was reconstituted with vehicle-treated PMN (+PMN) or IL-6-treated PMN (+PMN+IL6) and aggregation induced by thrombin receptor activating peptide. Supernatant was collected from aggregometry samples 5 minutes after TRAP stimulation by centrifugation at 10000 g. Cathepsin G in sample supernatants was determined from Western blots. *P<0.01 vs. −PMN, **P<0.01 vs. −PMN and +PMN

Neutrophil expression and release of cathepsin G in the absence and presence of IL-6 pre-treatment was examined. Briefly, neutrophils were isolated by histopaque density centrifugation and cultured in the absence or presence of IL-6 for 24 hours as described above. Neutrophil expression of cathepsin G was determined from lysates of IL-6-treated and vehicle-treated PMNs as follows: Cultured cells were washed, resuspended in lysis buffer (0.1% SDS, 150 mM NaCl, 50 mM Tris-HCl, 2 mM EDTA, 10 μg/ml aprotinin, 10 μg/ml leupeptin, 1 mM PMSF, 1 mM Na$_3$VO$_4$), and proteins separated by SDS-PAGE (10 μg protein/lane on 10% polyacrylamide gel). Proteins were transferred to nitrocellulose membranes and probed with goat-anti-human cathepsin G antibody (Santa Cruz Biotechnology) followed by HRP-conjugated rabbit anti-goat secondary antibody (Santa Cruz Biotechnology). Proteins were visualized by enhanced chemiluminescence and bands quantified by densitometry. Neutrophil release of cathepsin G was determined by Western blotting supernatants obtained from TRAP-stimulated aggregation samples of PRP alone, PRP reconstituted with vehicle-treated PMN, and PRP reconstituted with IL-6-treated PMN. Results demonstrate that IL-6 increases neutrophil expression of cathepsin G (FIG. 7A). Furthermore, neutrophils release cathepsin G in the presence of activated platelets, and release is enhanced by pre-treatment of PMNs with IL-6 (FIG. 7B).

Example 6

Figure 8:
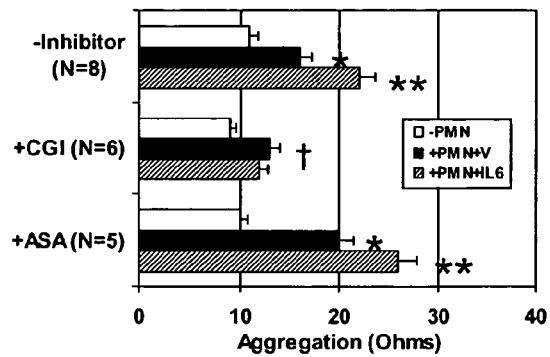
FIG. 8 depicts inhibition of cathepsin G, but not COX-1, mitigates the pro-aggregatory effect of IL6-treated neutrophils. Human neutrophils (PMN) were cultured with IL-6 (PMN+IL6) or vehicle (PMN+V) for 24 hours as described. Platelet rich plasma was reconstituted with vehicle or PMNs and aggregation in response to TRAP was determined in the presence of no inhibitor (−Inhibitor), cathepsin G inhibitor (+CGI), or aspirin (+ASA) *P<0.01 vs. −PMN, **P<0.01 vs. −PMN and +PMN+V, †P<0.05 vs. −PMN.

Inhibition of Cathepsin G Attenuates the Ability of Neutrophils to Augment Platelet Aggregation In Vitro Cathepsin G is a known platelet agonist[23] and candidate molecule to mediate the pro-aggregatory effect of neutrophils on platelets. The effect of the cathepsin G inhibitor, Z-Gly-Leu-Phe-CMK (100 μM for 20 min in vitro, Sigma-Aldrich Co, St. Louis, Mo.)[29], on TRAP-induced platelet aggregation was examined in the presence and absence of vehicle-treated and IL-6-treated neutrophils. Cathepsin G inhibition prevented IL-6-treated neutrophils from augmenting aggregation compared to vehicle-treated neutrophils (FIG. 8). Aggregation in the presence of vehicle-treated neutrophils was attenuated compared but remained greater than in PRP alone (FIG. 8). Because platelet-neutrophil interactions can enhance platelet thromboxane production[19, 30], the effect of aspirin, which inhibits cyclooxygenase-1 (COX-1)-dependent platelet aggregation and thromboxane production[31] was evaluated, on aggregation in the presence of vehicle-treated and IL-6-treated neutrophils. In these experiments, samples were incubated with 30 μM aspirin for 20 minutes prior to inducing platelet aggregation with TRAP. (30 μM aspirin approximates plasma concentrations after a 325 mg oral dose[32] and abolished arachidonic acid-induced platelet aggregation in preliminary experiments.) The presence of aspirin did not alter the pro-aggregatory effect of vehicle-treated neutrophils nor did it alter the ability of IL-6-treated neutrophils to further enhance platelet aggregation. These experiments indicate that the pro-aggregatory effect of neutrophils can be mitigated by inhibition of cathepsin G but not COX-1. The data also suggest that interaction of neutrophils with platelets may be a potential pathway for platelet aspirin resistance, particularly when neutrophils are under the inflammatory influence of IL-6, as commonly occurs in the settings of myocardial infarction and after trauma or surgery.

Example 7

Inhibition of Cathepsin G Delays Thrombus Formation In Vivo

Figure 9:
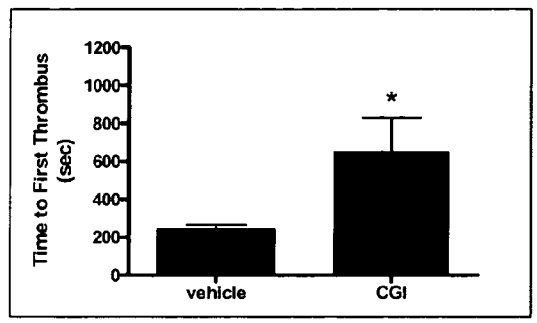
FIG. 9 demonstrates that inhibition of cathepsin G delays microvascular thrombus formation in vivo in the mouse. Anesthetized C57BL6/J mice were injected intravenously with the cathepsin G inhibitor (CGI)-Z-Gly-Leu-Phe-CMK (50 μl of 4 mM solution). Leukocytes were labeled in vivo with rhodamine-6-G, and mesenteric microvascular injury was induced with ferric chloride (500 μM). Time to first thrombus formation (>10 μm) was determined from digital images. N=7 vehicle and 7 CGI-treated, *P<0.05.

C57BL6/J mice were anesthetized with ketamine/xylazine and injected intravenously with an inhibitor of cathepsin G, Z-Gly-Leu-Phe-CMK (50 μl of 4 mM solution to achieve ~100 μM in vivo), or vehicle. Mice were also injected with rhodamine-6-G to label circulating leukocytes. Mesentery was exteriorized through a midline abdominal incision, and arteriolar injury was induced with topical application of 500 μM ferric chloride. Time to first thrombus formation was determined from digital images obtained using intravital fluorescence microscopy as described above. Results from these experiments are shown in FIG. 9 and show that inhibition of cathepsin G diminishes capacity for thrombus formation in vivo.

Example 8

Role of Neutrophils in Hemostasis In Vivo

Figure 10:
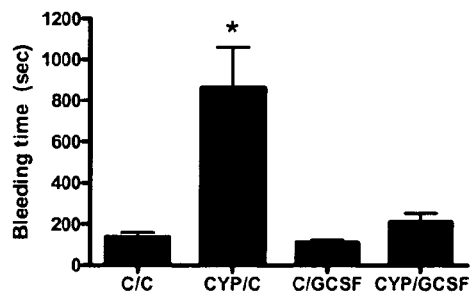
FIG. 10 depicts neutrophil counts and in vivo hemostasis. Mice were injected intraperitoneally with cyclophosphamide (CYP, 50 mg/kg) or vehicle (C), followed 24 hours later by 3 consecutive days of subcutaneous injection of granulocyte colony stimulating factor (GCSF, 1 μg) or vehicle (C). Three days after CYP injection, bleeding times were assessed in anesthetized mice after amputating the distal 3 mm section of tail. Time to visual cessation of bleeding was recorded. N=16 (4 each condition); bleeding times were significantly different by one way ANOVA (P<0.001), *P<0.01 vs. all other conditions by Bonferroni corrected post hoc test.

Previous experiments demonstrated that in vivo depletion of neutrophils by injection of an anti-neutrophil antibody (Gr-1) prolonged tail bleeding time in mice. This observation was further tested by in vivo manipulation of neutrophil counts after injection of cyclophosphamide (CYP) and granulocyte colony stimulating factor (G-CSF). Briefly, C57BL6/J mice were treated with a single intraperitoneal injection of CYP (50 mg/kg or control vehicle) followed by daily subcutaneous injection of G-CSF (1 μg or control vehicle) for 3 days. Three days after CYP injection, tail bleeding time was assessed in anesthetized mice (ketamine 100 mg/kg intramuscular injection). Leukocyte counts were determined by automated cell counting and manual differential. CYP markedly reduced neutrophil counts and G-CSF treatment increased them (1.37±0.26, 0.14±0.03, 3.51±0.10, and 0.80±0.16×$10^3$/μl for vehicle/vehicle, CYP/vehicle, vehicle/G-CSF, and CYP/G-CSF, respectively). CYP treatment markedly prolonged bleeding time (FIG. 10), and G-CSF treatment in the absence of CYP shortened bleeding time. G-CSF treatment of CYP-treated mice restored bleeding time to baseline (FIG. 10). Neutrophil counts were highly correlated with bleeding time (r=−0.80, P<0.001). These data strongly support the concept that the number of circulating neutrophils plays an important physiologic role in hemostasis in vivo.

Example 9

Figure 11:
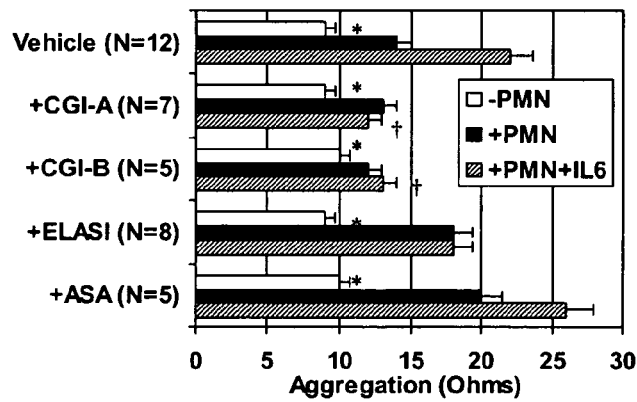
FIG. 11 depicts that cathepsin G inhibition specifically antagonizes the ability of IL-6-treated neutrophils to enhance platelet aggregation. Human neutrophils (PMN) were cultured with IL-6 (PMN+IL6) or vehicle (PMN) for 24 hours. Platelet aggregation in the presence (+PMN) and absence (−PMN) was measured in response to TRAP in the presence of vehicle (DMSO 1%) or the indicated inhibitor. CGI-A=cathepsin G inhibitor A (100 M Z-Gly-Leu-Phe-CMK), CGI-B=cathepsin G inhibitor B (500 nM $C_{36}H_{33}N_2O_6P$), ELASI=elastase inhibitor (100 M methoxy succinyl Ala-Ala-Pro-Ala-CMK (SEQ ID NO: 21)), and ASA=aspirin (30 M). *P<0.01 for intra-experiment effect of condition (−PMN, +PMN, PMN+IL6) on aggregation by one way ANOVA, ÷P<0.01 vs. vehicle/+PMN+IL6 by Bonferroni corrected post-hoc test.

Cathepsin G Inhibition Specifically Antagonizes the Proaggregatory Effect of IL-6-Treated Neutrophils Increased numbers of circulating neutrophils are often encountered in the pathophysiologic setting of an acute inflammatory stimulus, and IL-6 is the primary cytokine mediator of the acute phase response. We previously demonstrated that inhibition of cathepsin G with Z-Gly-Leu-Phe-chloromethyl ketone attenuated the proaggregatory effect of IL-6-treated neutrophils on platelet function in vitro. We have expanded on these initial findings by demonstrating that the effect of cathepsin G inhibition is specific, in that it is reproduced by a structurally unrelated cathepsin G inhibitory compound (Cathepsin G Inhibitor I, Calbiochem [$C_{36}H_{33}N_2O_6P$]), but not by a chloromethyl ketone elastase inhibitor (methoxy succinyl Ala-Ala-Pro-Ala-CMK (SEQ ID NO: 21), Calbiochem) or aspirin (FIG. 11). Interestingly, elastase inhibition (P=0.07) and aspirin (P=0.03) increased the pro-aggregatory effect of vehicle treated PMNs and did not significantly reduce the ability of IL-6-treated PMNs to enhance aggregation.

These data support the concept that neutrophils enhance platelet-mediated thrombus formation under inflammatory conditions, and this effect is specifically antagonized by cathepsin G inhibition. Moreover, elevated leukocyte counts reduce the anti-aggregatory and anti-thrombotic efficacy of aspirin; and, the cathepsin G inhibitor, $C_{36}H_{33}N_2O_6P$, is a potent and effective inhibitor of pro-thrombotic effects, both in vitro and in vivo.

Example 10

Effects of Aspirin and $C_6H_{33}N_2O_6P$ on Platelet Aggregation In Vitro in the Presence of Increasing Numbers of Neutrophils Observational studies have demonstrate an increased risk of MI and stroke after acute inflammatory illnesses[1]. Such a phenomenon could be explained by either the induction of a prothrombotic state or a reduction in the efficacy of standard anti-thrombotic treatment, or both. The gold-standard anti-platelet therapy used for both primary and secondary cardiovascular protection is aspirin[33, 34]. A number of authors have suggested that inflammation might mitigate aspirin's ability to inhibit platelet activation[35, 36], but the mechanism for the proposed decrement in aspirin's antiplatelet action has not been determined. Our previous experiments had already demonstrated that neutophils can promote a pro-thrombotic state by enhancing platelet reactivity. We next tested the hypothesis that the antiplatelet effect of aspirin would diminish under conditions of increasing neutrophil numbers and contrasted aspirin results with the antiplatelet effects of the cathepsin G inhibitor, $C_{36}H_{33}N_2O_6P$, under the same pro-inflammatory conditions.

A series of experiments were conducted in which the ability of aspirin and $C_{36}H_{33}N_2O_6P$ to inhibit platelet aggregation was tested in vitro in the presence of neutrophil concentrations through a range of physiologic to pathologic. Neutrophils were isolated and cultured for 24 hours as already described above. Neutrophils were then reconstituted at escalating concentrations with freshly prepared platelet rich plasma (PRP, 170×$10^3$ platelets/μl. TRAP-induced platelet activation was determined by impedance aggregometry in the absence and presence of aspirin (30 μM) or $C_{36}H_{33}N_2O_6P$ (500 nM).

Figure 12:
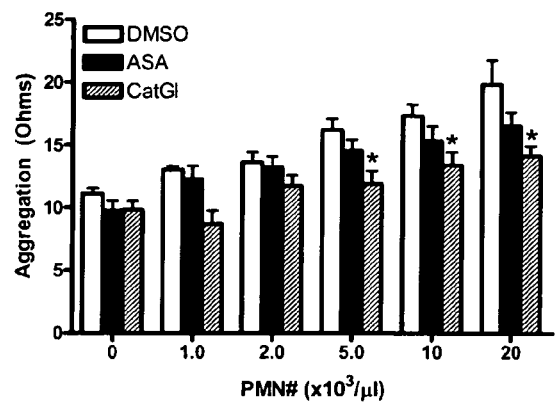
FIG. 12 demonstrates that $C_{36}H_{33}N_2O_6P$ but not aspirin inhibits the pro-aggregatory effect of increasing numbers of neutrophils in vitro. Human neutrophils (PMN) were isolated by histopaque centrifugation and cultured in RPMI/5% human serum for 24 hours. Neutrophils were reconstituted with freshly prepared platelet rich plasma, and impedance aggregometry (in response to 15 μM TRAP) was assessed in the absence (0) or presence of increasing concentrations of PMNs, and the presence of DMSO (1%), aspirin (ASA, 30 μM), or $C_{36}H_{33}N_2O_6P$ (CatGI, 500 nM). N=7; significant main effects for leukocyte count and drug condition by 2-way ANOVA (P<0.0001), *P<0.05 vs. DMSO by Bonferroni corrected post-hoc test.

A progressive increase in platelet aggregation was observed in the presence of DMSO-vehicle (P<0.001, FIG. 12) similar to what was observed in the experiments depicted in FIG. 1. Aggregation also increased with increasing neutrophil count in samples incubated with aspirin. Although this effect appeared less pronounced than with vehicle, there was no significant difference between vehicle and aspirin-treated samples at any of the neutrophil concentrations. In contrast, aggregation was decreased in samples incubated with the cathepsin G inhibitor, $C_{36}H_{33}N_2O_6P$, and this effect increased with increasing neutrophil concentrations, reaching significance at 5, 10, and 20×$10^3$ neutrophils/μl (P<0.05, by Bonferonni corrected post-hoc test). Thus, the data demonstrate that aspirin has limited ability to suppress the pro-aggregatory influence of neutrophils on platelet function, but $C_{36}H_{33}N_2O_6P$ provides effective suppression of neutrophil-related platelet activation at nanomolar concentrations.

Example 11

Effects of Aspirin and $C_{36}H_{33}N_2O_6P$ on Clot Formation In Vivo in the Presence of Increasing Numbers of Neutrophils The ability of aspirin and $C_{36}H_{33}N_2O_6P$ to inhibit clot formation in vivo was tested under baseline conditions and after pharmacologically increasing the number of circulating neutrophils. Mice were treated for 3 consecutive days by SQ injection of vehicle or GCSF (1 μg). After the third injection, mice were anesthetized and injected intravenously (by retroorbital puncture) with vehicle (DMSO) or aspirin (50 μl of 1000 μM solution), or, in a second series of experiments, mice were injected IV with vehicle (DMSO) or $C_{36}H_{33}N_2O_6P$ (50 μl of 20 μM solution). In each experimental series, bleeding time was determined 30 minutes after IV injection after amputating the distal 3 mm section of tail.

Figure 13:
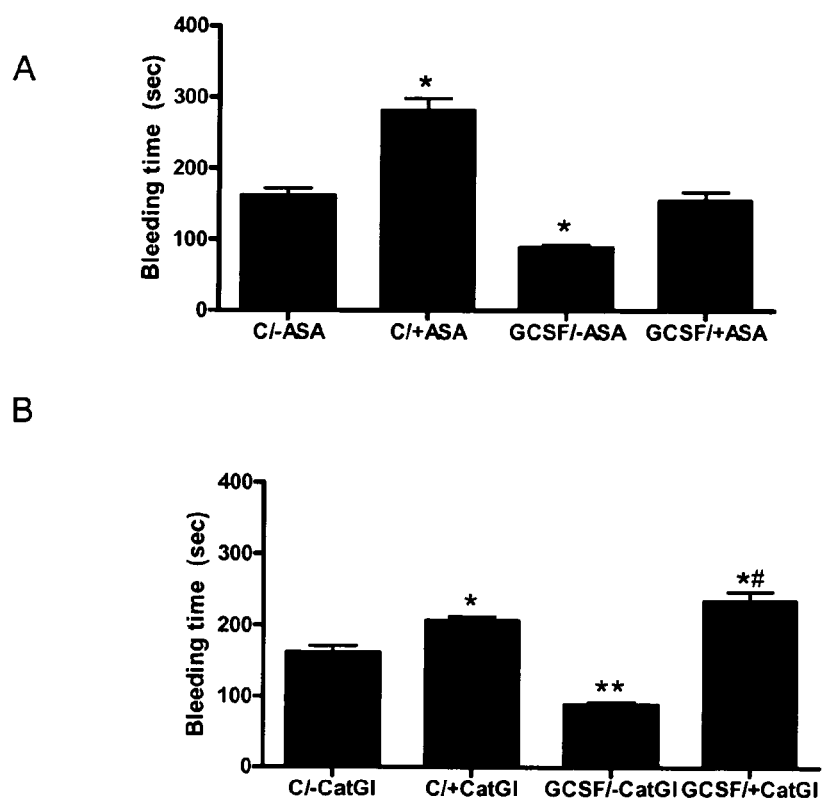
FIG. 13 demonstrates that $C_{36}H_{33}N_2O_6P$ is more effective than aspirin at inhibiting the pro-thrombotic effect of neutrophilia in vivo. Mice received 3 consecutive days of subcutaneous injection of granulocyte colony stimulating factor (GCSF, 1 μg) or vehicle (C). On the third day bleeding times were assessed in anesthetized mice 30-min after intravenous injection of the indicated inhibitor of platelet aggregation. Time to visual cessation of bleeding was recorded after amputating the distal 3 mm section of tail. A. Bleeding times were assessed in the presence of aspirin vehicle (−ASA) and aspirin (+ASA). N=30 (6-8 each condition); bleeding times were significantly different by one way ANOVA (P<0.0001), *P<0.05 vs. other conditions in A by Bonferroni corrected post hoc test. B. Bleeding times were assessed in the presence of $C_{36}H_{33}N_2O_6P$ vehicle (−CatGI) and $C_{36}H_{33}N_2O_6P$ (+CatGI). N=32 (8 each condition); bleeding times were significantly different by one may ANOVA (P<0.0001), *P<0.05 vs. C/−CatGI and GCSF/−CatGI by Bonferroni corrected post hoc test, **P<0.05 vs. other conditions in B by Bonferroni corrected post-hoc test, #P<0.05 vs. GCSF/+ASA.

GCSF significantly increased the number of blood neutrophils (1.20±0.35, 1.05±0.70, 4.90±1.25, and 5.24±1.34× $10^3$/μl for vehicle/vehicle, vehicle/inhibitor, GCSF/vehicle, and GCSF/inhibitor, respectively; P<0.0001 by ANOVA) on the third treatment day. As expected, mice treated with vehicle for GCSF and aspirin had longer bleeding times than mice treated with both vehicles (FIG. 13A). GCSF treatment in the absence of aspirin led to shorter bleeding time (i.e. earlier clot formation) compared to vehicle/vehicle-treated controls. Mice treated with both GCSF and aspirin had bleeding times that were no different from vehicle/vehicle controls and were significantly shorter than those seen in animals treated with aspirin and vehicle for GCSF; however, bleeding time was longer in this group compared to the group treated with GCSF and without aspirin. Results with aspirin contrast with those for the cathepsin G inhibitor (FIG. 13B). Vehicle/$C_{36}H_{33}N_2O_6P$ treatment prolonged bleeding time, and GCSF/vehicle treatment shortened bleeding time compared to vehicle/vehicle controls similar to results seen with aspirin. However, mice treated with both GCSF and $C_{36}H_{33}N_2O_6P$ had longer bleeding times than vehicle/vehicle controls and GCSF/aspirin treated animals (FIG. 13B).

These data demonstrate that neutrophilia mitigates the antithrombotic efficacy of aspirin in vivo and that under such pro-inflammatory conditions, the cathepsin G inhibitor, $C_{36}H_{33}N_2O_6P$, provides more effective and more potent inhibition of clot formation than aspirin.

Example 12

Figure 14:
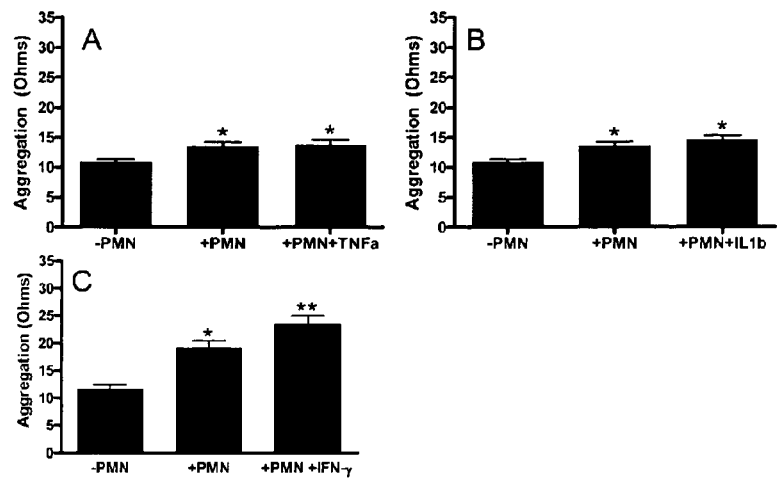
FIG. 14 depicts the effect of cytokines on neutrophil-dependent platelet aggregation in vitro. Human neutrophils (PMN) were isolated by histopaque centrifugation and cultured in RPMI/5% human serum for 24 hours in the presence of the indicated cytokine (10 ng/ml) or vehicle. Platelet rich plasma was freshly prepared from the same donor, and impedance aggregometry (in response to 15 μM TRAP) was performed in the absence (—PMN) or presence of vehicle-treated (+PMN) or cytokine-treated PMN (+PMN+cytokine). A. TNFα (N=7). B. IL-1β (N=7). C. Inteferon-gamma (N=9). *P<0.05 vs. −PMN, **P<0.05 vs. − PMN and +PMN by Bonferroni corrected post-hoc test.

TNFα, IL-1β and INFγ and their Impact on Neutrophil-Dependent Platelet Activation Previous studies demonstrated that IL-6 enhanced the ability of neutrophils to augment platelet aggregation. We tested whether this effect could be reproduced by other pro-inflammatory cytokines. Neutrophils were isolated and cultured in the absence and presence of tumor necrosis factor-alpha (TNFα, 10 ng/ml), interleukin 1-beta (IL-1β, 10 ng/ml), or interferon-gamma (INFγ, 10 ng/ml) for 24 hours as already described above. Neutrophils were then reconstituted with freshly prepared PRP (170×$10^3$ platelets/μl) and aggregation to TRAP and collagen was assessed using impedance aggregometery. In contrast to IL-6, TNFα and IL-1β did not modify the effect of PMN on platelet aggregation (FIG. 14). However, INFγ treatment enhanced the pro-aggregatory effect of PMNs on platelet aggregation (FIG. 14) similar to what was observed with IL-6. Results were the same when collagen was used as the agonist instead of TRAP.

Example 13

Inhibition of JAK/STAT Signaling Mitigates the Impact of IL-6 and INFγ on PMN-Dependent Platelet Aggregation IL-6 and INFg are pleiotropic cytokine signaling molecules that alter the phenotype of target cells through cell surface receptor-mediated modulation of gene expression. Binding of either IL-6 or INFγ to its specific receptor causes activation of Janus kinases (JAKs) and signal transducers and activators of transcription (STAT1/3 and STAT1 for IL-6 and INFγ, respectively). Signal transduction through IL-6[37], INFγ[38], and JAK/STAT[39] has been reviewed in detail elsewhere.

Figure 15:
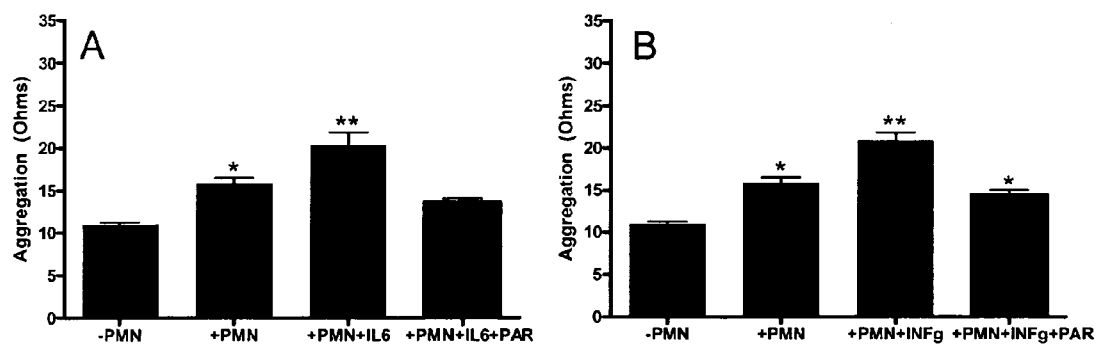
FIG. 15 depicts that parthenolide inhibits the proaggregatory effects of IL-6 and INFγ. Human neutrophils (PMN)

The effect of parthenolide, an inhibitor of STAT1/3 activation and IL-6-induced gene transcription[40], on the ability of IL-6- and INFγ-treated neutrophils to augment aggregation was investigated. For these experiments, isolated neutrophils were incubated in the presence or absence of IL-6 (10 ng/ml) and parthenolide (5 μM) for 24 hours. TRAP-induced aggregation of neutrophil-PRP suspensions was assessed by impedance aggregometry as described above. Parthenolide had no effect on cell viability which remained >95% at 24 hours. The data demonstrate that treatment of neutrophils with IL-6 or INFγ increases TRAP-induced aggregation and that co-incubation of cytokine-treated neutrophils with parthenolide prevents this increase (FIG. 15).

Example 14

STAT1α Mediates the Pro-Aggregatory Effect of Neutrophilic Cells and IL-6

HL60 cells are an immortalized leukemic cell line in the myeloid lineage that can be induced into terminal granulocytic differentiation by dimethyl sulfoxide (DMSO)[41] and are capable of exogenous gene expression. HL60 cells have been extensively used to investigate neutrophil structure and function (see Collins SJ[41] for review). Stably transfected HL60 cell lines that overexpress STAT1α and its dominant negative STAT1β were created to investigate the role of STAT1 in neutrophil-dependent platelet activation. Briefly, STAT1α and STAT1β were subcloned from pRc/CMC plasmids into pIRES2-EGFP plasmids containing a Kanomycin/Neomycin resistance cassette. A 2364 bp sequence of the STAT1α gene was inserted into the pIRES2-EGFP vector between NheI and SacII sites. A 2138 bp sequence of the alternatively spliced STAT1β gene was inserted into the pIRES2-EGFP vector between EcoRI and BamHI sites. The correct fragments for each gene sequence and orientation were verified by enzymatic mapping and DNA sequence analysis. HL60 cells were transfected with pIRES2-EGFP-STAT1α and pIRES2-EGFP-STAT1β plasmids by electroporation (300V and 960 μF) and cells grown in G418 (500 μg/ml) containing selection media. Stable transfection of HL60 cells with exogenous gene expression was verified by fluorescence microscopy and flow cytometry.

To determine the impact of STAT1 expression on the ability of HL60 cells to modify platelet aggregation, platelet aggregation was evaluated in mixed platelet-HL60 cell suspensions using a modified version of our PMN aggregation protocol. Briefly, HL60 cells (with and without plasmid transfection) were cultured in RPMI/20% fetal calf serum (+G418 for transfected cells). Cells in log-phase growth were incubated with 1.5% dimethyl sulfoxide (DMSO) for a total of 96 hours to induce neutrophil differentiation[41]. After the initial 48 hours of DMSO treatment, cells were incubated in the presence or absence of IL-6 (10 ng/ml) for an additional 48 hours. At the end of 96-hour treatment period, HL60 cells were harvested (cell viability >90% by trypan blue exclusion in native and transfected cell lines) and reconstituted with freshly prepared PRP ($170 \times 10^3$ platelets/μl). Impedance aggregometry in response to TRAP and collagen were then determined in similar fashion described for PMNs.

HL60 cells recapitulated the pro-aggregatory phenotype observed with PMNs (FIG. 16). DMSO-treated cells increased platelet aggregation compared to PRP alone, and treatment with IL-6 further increased this effect. As predicted, these effects were exaggerated in HL60 cells transfected with STAT1α and diminished in cells transfected with the dominant negative STAT1β (FIG. 16). Similar results were seen when collagen was used as the agonist instead of TRAP. These results indicate that STAT1α is a critical mediator of the pro-aggregatory effects exerted by the neutrophilic cell line HL60 and exposure to IL-6.

CONCLUSIONS

In summary, the data presented herein demonstrate a role for neutrophils in hemostatic processes in vitro and vivo; and, specifically a pro-thrombotic role for neutrophil cathepsin G. Furthermore, the data demonstrate that inhibition of cathepsin G reduces platelet aggregability in vitro and thrombus formation in vivo. These novel findings indicate a that neutrophils participate in clot formation under normal physiologic and pro-inflammatory conditions, and demonstrate the necessity for the development of cathepsin G inhibitors, and other molecules that interfere with neutrophil (or monocyte) directed thrombus formation, as clinical antithrombotic agents.

REFERENCES

1. Smeeth L, Thomas S L, Hall A J, Hubbard R, Farrington P, Vallance P. Risk of myocardial infarction and stroke after acute infection or vaccination. N Engl J. Med. 2004; 351:2611-2618.
2. Danesh J, Collins R, Peto R. Chronic infections and coronary heart disease: is there a link? Lancet. 1997; 350:430-436.
3. Ridker P M, Cushman M, Stampfer M J, Tracy R P, Hennekens C H. Inflammation, aspirin, and the risk of cardiovascular disease in apparently healthy men. N Engl J. Med. 1997; 336(14):973-979.
4. Danesh J, Wheeler J G, Hirschfield G M, Eda S, Eiriksdottir G, A. R, Lowe G D O, Pepys M B, Gudnason V. C-reactive protein and other circulating markers of inflammation in the prediction of coronary heart disease. N Engl J. Med. 2004; 350:1387-1397.
5. Madjid M, Awan I, Willerson J T, Casscells S W. Leukocyte count and coronary heart disease. J Am Coll Cardiol. 2004; 44:1945-1956.
6. Grau A J, Boddy A W, Dukovic D A, Buggle F, Lichy C, Brandt T, Hacke W, CAPRIE I. Leukocyte count as an independent predictor of recurrent ischemic events. Stroke. 2004; 35:1147-1152.
7. Home B D, Anderson J L, John J M, Weaver A, Bair T L, Jensen K R, Renlund D G, Muhlestein J B, IHC Study G. Which white blood cell subtypes predict increased cardiovascular risk? J Am Coll Cardiol. 2005; 45:1638-1643.
8. Buffon A, Biasucci L M, Liuzzo G, D'Onofrio G, Crea F, Maseri A. Widespread coronary inflammation in unstable angina. N Engl J. Med. 2002; 347:5-12.
9. Brennan M-L, Penn M S, Van Lente F, Nambi V, Shishehbor M H, Aviles R J, Goormastic M, Pepoy M L, McErlean E S, Topol E J, Nissen S E, Hazen S L. Prognostic value of myeloperoxidase in patients with chest pain. N Engl J. Med. 2003; 349:1595-1604.
10. Ridker P M, Rifai N, Stampfer M J, Hennekens C H. Plasma concentration of interleukin-6 and the risk of future myocardial infarction among apparently healthy men. Circulation. 2000; 101:1767-1772.
11. Lindmark E, Diderholm E, Wallentin L, Siegbahn A. Relationship between interleukin 6 and mortality in patients with unstable coronary artery disease: effects of an early invasive or noninvasive strategy. JAMA. 2001; 286:2107-2113.
12. Cerletti C, Evangelista V, Mollino M, de Gaetano G. Platelet activation by polymorphonuclear leukocytes: Role of cathepsin G and P-selectin. Thromb Haemost. 1995; 74:218-223.
13. Palabrica T, Lobb R, Furie B C, Aronovitz M, Benjamin C, Hsu Y-M, Sajer S A, Furie B. Leukocyte accumulation promoting fibrin deposition is mediated in vivo by P-selectin on adherent platelets. Nature. 1992; 359:848-851.
14. Moir E, Booth N A, Bennett B, Robbie L A. Polymorphonuclear leucocytes mediate endogenous thrombus lysis via a u-PA-dependent mechanism. Br J. Haematol. 2001; 113:72-80.
15. Salvemini D, de Nucci G, Gryglewski R J, Vane J R. Human neutrophils and mononuclear cells inhibit platelet aggregation by releasing a nitric oxide-like factor. Proc Natl Acad Sci, USA. 1989; 86:6328-6332.
16. Koziak K, Sevigny J, Robson S C, Siegel J B, Kaczmarek E. Analysis of CD39/ATP diphosphohydrolase (ATPDase) expression in endothelial cells, platelets, and leukocytes. Thromb Haemost. 1999; 82:1538-1544.
17. Kerr R. Interleukin 6 and hemostasis. Br J. Haematol. 2001; 115:3-12.
18. Johnson J L, Moore E E, Tamura D Y, Zallen G, Biffl W L, Silliman C C. Interleukin-6 augments neutrophil cytotoxic potential via selective enhancement of elastase release. J Surg Res. 1998; 76:91-94.
19. Faraday N, Scharpf R B, Dodd-o J M, Martinez E A, Rosenfeld B A, Dorman T. Leukocytes can enhance platelet-mediated aggregation and thromboxane release via interaction of P-selectin glycoprotein ligand 1 with P-selectin. Anesthesiology. 2001; 94:145-151.
20. Hirano T. The biology of interleukin-6. Chem. Immunol. 1992; 51:153-180.
21. Morrell C N, Matsushita K, Chiles K, Scharpf R B, Yamakuchi M, Mason R J, Bergmeier W, Mankowski J L, Baldwin W M, Faraday N, Lowenstein C J. Regulation of platelet granule exocytosis by S-nitrosylation. Proc Natl Acad Sci USA. 2005; 102:3782-3787.
22. Ishikawa M, Stokes K Y, Zhang J H, Nanda A, Granger D N. Cerebral microvascular responses to hypercholesterolemia: roles of NADPH oxidase and P-selection. Circ Res. 2004; 94:239-244.

23. Selak M A, Chignard M, Smith J B. Cathepsin G is a strong platelet agonist released by neutrophils. Biochem J. 1988; 251:293-299.
24. Renesto P, Chignard M. Tumor necrosis factor-a enhances platelet activation via cathepsin G released from neutrophils. J. Immunol. 1991; 146:2305-2309.
25. Sambrano G R, Huang W, Faruqi T, Mahrus S, Craik C, Coughlin S R. Cathepsin G activates protease-activated receptor-4 in human platelets. J Biol. Chem. 2000; 275: 6819-6823.
26. Hidari K I, Weyrich A S, Zimmerman G A, McEver R P. Engagement of P-selectin glycoprotein ligand-1 enhances tyrosine phosphorylation and activates mitogen-activated protein kinases in human neutrophils. J Biol. Chem. 1997; 272:28750-28756.
27. Evangelista V, Manarini S, Sideri R, Rotondo S, Martelli N, Piccoli A, Totani L, Piccardoni P, Vestweber D, de Gaetano G, Cerletti C. Platelet/polymorphonunclear leukocyte interaction: P-selectin triggers protein-tyrosine phosphorylation-dependent CD11b/CD18 adhesion: role of PSGL-1 as a signaling molecule. Blood. 1999; 93:876-885.
28. Rainger G E, Rowley A F, Nash G B. Adhesion-dependent release of elastase from human neutrophils in a novel, flow-based model: Specificity of different chemotactic agents. Blood. 1998; 92:4819-4827.
29. Goel M S, Diamond S L. Neutrophil enhancement of fibrin deposition under flow through platelet-dependent and -independent mechanisms. Arterioscler Thromb Vasc Biol. 2001; 21:2093-2098.
30. Maugeri N, Evangelista V, Piccardoni P, Dell'Elba G, Celardo A, de Gaetano G, Cerletti C. Transcellular metabolism of arachidonic acid: increased platelet thromboxane generation in the presence of activated polymorphonuclear leukocytes. Blood. 1992; 80:447-451.
31. Vane JR. Inhibition of prostaglandin synthesis as a mechanism of action for aspirin-like drugs. Nature New Biol. 1971; 231:232-235.
32. Feldman M, Cryer B. Aspirin absorption rates and platelet inhibition times with 325-mg buffered aspirin tablets (chewed or swallowed intact) and with buffered aspirin solution. Am J. Cardiol. 1999; 84:404-409.
33. Antithrombotic Trialists' Collaboration. Collaborative meta-analysis of randomised trials of antiplatelet therapy for prevention of death, myocardial infarction, and stroke in high risk patients. Br Med J. 2002; 324:71-86.
34. Hayden M, Pignone M, Phillips C, Mulrow C. Aspirin for the primary prevention of cardiovascular events: A summary of the evidence for the U.S. Preventive Services Task Force. Ann Intern Med. 2002; 136:161-172.
35. McKee S A, Sane D C, Deliargyris E N. Aspirin resistance in cardiovascular disease: A review of prevalence, mechanisms, and clinical significance. Thromb Haemost. 2002; 88:711-715.
36. Hankey G J, Eikelboom J W. Aspirin resistance. Lancet. 2006; 367:606-617.
37. Heinrich P C, Behrmann I, Haan S, Hermanns H M, Muller-Newen G, Schaper F. Principles of interleukin (IL)-6-type cytokine signalling and its regulation. Biochem J. 2003; 374:1-20.
38. Boehm U, Klamp T, Groot M, Howard J C. Cellular responses to interferon-g. Annu Rev Immunol. 1997; 15:749-795.
39. Kisseleva T, Bhattacharya S, Braunstein J, Schindler C W. Signaling through the JAK/STAT pathway, recent advances and future challenges. Gene. 2002; 285:1-24.
40. Sobota R, Szwed M, Kasza A, Bugno M, Kordula T. Parthenolide inhibits activation of signal transducers and activators of transcription (STATs) induced by cytokines of the IL-6 family. Biochem Biophys Res Commun. 2000; 267:329-333.
41. Collins S J. The HL-60 promyelocytic leukemia cell line: Proliferation, differentiation, and cellular oncogene expression. Blood. 1987; 70:1233-1244.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting platelet aggregation or clot formation in a subject, comprising:
   identifying a subject that has previously shown resistance or failure to respond to aspirin treatment for inhibiting platelet aggregation or clot formation; and
   administering to the subject an amount of a cathepsin G inhibitor selected from the group consisting of Z-gly-leu-phe-chloromethyl ketone, Gly-Leu-Phe, benzyloxycarbonyl-Gly-Leu-Phe-chloromethyl ketone, SEQ ID NO: 9, SEQ ID NO: 10, SEQ ID NO: 11, SEQ ID NO: 12, SEQ ID NO: 13, SEQ ID NO: 15, monocyte neutrophil elastase inhibitor, maspin, secretory leukocyte protease inhibitor, SEQ ID NO: 16, SEQ ID NO: 17, SEQ ID NO: 18, SEQ ID NO: 19, SEQ ID NO: 20, β-ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3 and Ac-Ala-Ala-ANle-OE effective to inhibit platelet aggregation or clot formation in the subject;
   thereby inhibiting platelet aggregation or clot formation in the subject.

2. The method of claim 1, wherein the cathepsin G is produced by neutrophils.

3. The method of claim 1, wherein the subject has experienced tissue injury from surgery or accidental trauma.

4. The method of claim 1, wherein the subject has an acute bacterial or viral infection selected from the group consisting of pneumonia, bronchitis, urinary tract infection, and sepsis.

5. The method of claim 1, wherein the subject has undergone a microvascular surgical reconstructive procedure.

6. The method of claim 1, wherein the subject is receiving granulocyte colony stimulating factor therapy.

7. The method of claim 1, wherein the subject is receiving stem cell therapy.

8. The method of claim 1, wherein the subject has sickle cell anemia.

9. The method of claim 1, wherein the subject has a vascular occlusive disease selected from the group consisting of a heart attack, myocardial infarction, unstable angina, stroke, peripheral arterial occlusive disease or thromboembolism, venous thromboembolism, thromboembolism of a coronary artery bypass graft, coronary artery stent, native carotid artery after surgical endarterectomy, carotid artery stent, renal artery bypass graft, renal artery stent, subclavian artery bypass graft, subclavian artery stent, aortic artery graft, aortic artery stent, iliac artery bypass graft, iliac artery stent, femoral artery bypass graft, femoral artery stent, peripheral artery bypass graft, or peripheral artery stent.

10. A method of inhibiting platelet aggregation or clot formation in a subject, comprising:
    identifying a subject that has previously shown resistance or failure to respond to aspirin treatment or has an acute or chronic inflammatory state identified as aspirin resistance as defined by a peripheral blood total leukocyte count greater than 7000/μl or a peripheral blood neutrophil count greater than 4000/μl; and
    administering to the subject an amount of a cathepsin G inhibitor selected from the group consisting of Z-gly-leu-phe-chloromethyl ketone, Gly-Leu-Phe, benzyloxycarbonyl-Gly-Leu-Phe-chloromethyl ketone, SEQ ID NO: 9, SEQ ID NO: 10, SEQ ID NO: 11, SEQ ID NO: 12, SEQ ID NO: 13, SEQ ID NO: 15, monocyte neutrophil elastase inhibitor, maspin, secretory leukocyte protease inhibitor, SEQ ID NO: 16, SEQ ID NO: 17, SEQ ID NO: 18, SEQ ID NO: 19, SEQ ID NO: 20, β-ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3 and Ac-Ala-Ala-ANle-OE effective to inhibit platelet aggregation or clot formation in the subject;
    thereby inhibiting platelet aggregation or clot formation in the subject.

11. A method of inhibiting platelet aggregation or clot formation in a subject, comprising:
    administering to the subject an amount of a cathepsin G inhibitor selected from the group consisting of Gly-Leu-Phe, benzyloxycarbonyl-Gly-Leu-Phe-chloromethyl ketone, SEQ ID NO: 9, SEQ ID NO: 10, SEQ ID NO: 11, SEQ ID NO: 12, SEQ ID NO: 13, SEQ ID NO: 15, monocyte neutrophil elastase inhibitor, maspin, secretory leukocyte protease inhibitor, SEQ ID NO: 16, SEQ ID NO: 17, SEQ ID NO: 18, SEQ ID NO: 19, SEQ ID NO: 20, β-ketophosphonate 1 (JNJ-10311795; RWF-355871), Ac-Ala-Ala-ANva-OPh, Ac-Ala-Ala-ANle-OPh, Ac-Ala-Ala-ANle-OCH2CF3 and Ac-Ala-Ala-ANle-OE effective to inhibit platelet aggregation or clot formation in the subject, wherein the subject has previously shown resistance or failure to respond to aspirin treatment;
    thereby inhibiting platelet aggregation or clot formation in the subject.

* * * * *

SEQUENCE LISTING

```
<160> NUMBER OF SEQ ID NOS: 21

<210> SEQ ID NO 1
<211> LENGTH: 212
<212> TYPE: PRT
<213> ORGANISM: Homo sapiens

<400> SEQUENCE: 1

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
```

```
                65                  70                  75                  80
            Ser Lys Glu Ala Leu Ala Glu Asn Asn Leu Asn Leu Pro Lys Met Ala
                                85                  90                  95

Glu Lys Asp Gly Cys Phe Gln Ser Gly Phe Asn Glu Glu Thr Cys Leu
                        100                 105                 110

Val Lys Ile Ile Thr Gly Leu Leu Glu Phe Glu Val Tyr Leu Glu Tyr
                    115                 120                 125

Leu Gln Asn Arg Phe Glu Ser Ser Glu Glu Ala Arg Ala Val Gln
                130                 135                 140

Met Ser Thr Lys Val Leu Ile Gln Phe Leu Gln Lys Lys Ala Lys Asn
            145                 150                 155                 160

Leu Asp Ala Ile Thr Thr Pro Asp Pro Thr Thr Asn Ala Ser Leu Leu
                            165                 170                 175

Thr Lys Leu Gln Ala Gln Asn Gln Trp Leu Gln Asp Met Thr Thr His
                        180                 185                 190

Leu Ile Leu Arg Ser Phe Lys Glu Phe Leu Gln Ser Ser Leu Arg Ala
                    195                 200                 205

Leu Arg Gln Met
                210

<210> SEQ ID NO 2
<211> LENGTH: 1131
<212> TYPE: DNA
<213> ORGANISM: Homo sapiens

<400> SEQUENCE: 2
cattctgccc tcgagcccac cgggaacgaa agagaagctc tatctcccct ccaggagccc      60
agctatgaac tccttctcca caagcgcctt cggtccagtt gccttctccc tggggctgct     120
cctggtgttg cctgctgcct ccctgccccc agtaccccca ggagaagatt ccaaagatgt     180
agccgcccca cacagacagc cactcacctc ttcagaacga attgacaaac aaattcggta     240
catcctcgac ggcatctcag ccctgagaaa ggagacatgt aacaagagta acatgtgtga     300
aagcagcaaa gaggcactgg cagaaaacaa cctgaacctt ccaaagatgg ctgaaaaaga     360
tggatgcttc aatctggatt caatgaggag gacttgcctg gtgaaaatca tcactggtct     420
ttggagtttt gaggtatacc tagagtacct ccagaacaga tttgagagta gtgaggaaca     480
agccagagct gtgcagatga gtacaaaagt cctgatccag ttcctgcaga aaaaggcaaa     540
gaatctagat gcaataacca cccctgaccc aaccacaaat gccagcctgc tgacgaagct     600
gcaggcacag aaccagtggc tgcaggacat gacaactcat ctcattctgc gcagctttaa     660
ggagttcctg cagtccagcc tgagggctct tcggcaaatg tagcatgggc acctcagatt     720
gttgttgtta atgggcattc cttcttctgg tcagaaacct gtccactggg cacagaactt     780
atgttgttct ctatggagaa ctaaaagtat gagcgttagg acactatttt aattattttt     840
aatttattaa tatttaaata tgtgaagctg agttaattta tgtaagtcat atttatattt     900
ttaagaagta ccacttgaaa cattttatgt attagttttg aaataataat ggaaagtggc     960
tatgcagttt gaatatcctt tgtttcagag ccagatcatt tcttggaaag tgtaggctta    1020 cctcaaaataa atggctaact tatacatatt tttaaagaaa tatttatatt gtatttatat    1080
aatgtataaa tggttttat accaataaat ggcattttaa aaaattcagc a               1131

<210> SEQ ID NO 3
<211> LENGTH: 166
<212> TYPE: PRT
```

<213> ORGANISM: Homo sapiens

<400> SEQUENCE: 3

```
Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 4
<211> LENGTH: 1240
<212> TYPE: DNA
<213> ORGANISM: Homo sapiens

<400> SEQUENCE: 4

```
cacattgttc tgatcatctg aagatcagct attagaagag aaagatcagt taagtccttt      60
ggacctgatc agcttgatac aagaactact gatttcaact tctttggctt aattctctcg    120
gaaacgatga atatacaag ttatatcttg gcttttcagc tctgcatcgt tttgggttct     180
cttggctgtt actgccagga cccatatgta aagaagcag aaaaccttaa gaaatatttt     240
aatgcaggtc attcagatgt agcggataat ggaactcttt tcttaggcat tttgaagaat    300
tggaaagagg agagtgacag aaaaataatg cagagccaaa ttgtctcctt ttacttcaaa    360
ctttttaaaa actttaaaga tgaccagagc atccaaaaga gtgtggagac catcaaggaa    420
gacatgaatg tcaagttttt caatagcaac aaaaagaaac gagatgactt cgaaaagctg    480
actaattatt cggtaactga cttgaatgtc aacgcaaag caatacatga actcatccaa     540
gtgatggctg aactgtcgcc agcagctaaa acagggaagc gaaaaggag tcagatgctg     600
tttcgaggtc gaagagcatc ccagtaatgg ttgtcctgcc tgcaatattt gaattttaaa    660
tctaaatcta tttattaata tttaacatta tttatatggg aatatatttt ttagactcat    720
caatcaaata agtatttata atagcaactt ttgtgtaatg aaaatgaata tctattaata    780
tatgtattat ttataattcc tatatcctgt gactgtctca cttaatcctt tgttttctga    840
ctaattaggc aaggctatgt gattacaagg ctttatctca ggggccaact aggcagccaa    900
cctaagcaag atcccatggg ttgtgtgttt atttcacttg atgataccat gaacacttat    960
aagtgaagtg atactatcca gttactgccg gtttgaaaat atgcctgcaa tctgagccag   1020
```

```
tgctttaatg gcatgtcaga cagaacttga atgtgtcagg tgaccctgat gaaaacatag      1080
catctcagga gatttcatgc ctggtgcttc caaatattgt tgacaactgt gactgtaccc      1140
aaatggaaag taactcattt gttaaaatta tcaatatcta atatatatga ataaagtgta      1200
agttcacaac aaaaaaaaaa aaaaaaaaaa aaaaaaaaa                             1240
```

<210> SEQ ID NO 5
<211> LENGTH: 255
<212> TYPE: PRT
<213> ORGANISM: Homo sapiens

<400> SEQUENCE: 5

```
Met Gln Pro Leu Leu Leu Leu Ala Phe Leu Leu Pro Thr Gly Ala
 1               5                  10                  15

Glu Ala Gly Glu Ile Gly Gly Arg Glu Ser Arg Pro His Ser Arg
                20                  25                  30

Pro Tyr Met Ala Tyr Leu Gln Ile Gln Ser Pro Ala Gly Gln Ser Arg
            35                  40                  45

Cys Gly Gly Phe Leu Val Arg Glu Asp Phe Val Leu Thr Ala Ala His
 50                  55                  60

Cys Trp Gly Ser Asn Ile Asn Val Thr Leu Gly Ala His Asn Ile Gln
 65                  70                  75                  80

Arg Arg Glu Asn Thr Gln Gln His Ile Thr Ala Arg Arg Ala Ile Arg
                85                  90                  95

His Pro Gln Tyr Asn Gln Arg Thr Ile Gln Asn Asp Ile Met Leu Leu
            100                 105                 110

Gln Leu Ser Arg Arg Val Arg Arg Asn Arg Asn Val Asn Pro Val Ala
            115                 120                 125

Leu Pro Arg Ala Gln Glu Gly Leu Arg Pro Gly Thr Leu Cys Thr Val
130                 135                 140

Ala Gly Trp Gly Arg Val Ser Met Arg Arg Gly Thr Asp Thr Leu Arg
145                 150                 155                 160

Glu Val Gln Leu Arg Val Gln Arg Asp Arg Gln Cys Leu Arg Ile Phe
                165                 170                 175

Gly Ser Tyr Asp Pro Arg Arg Gln Ile Cys Val Gly Asp Arg Arg Glu
            180                 185                 190

Arg Lys Ala Ala Phe Lys Gly Asp Ser Gly Gly Pro Leu Leu Cys Asn
            195                 200                 205

Asn Val Ala His Gly Ile Val Ser Tyr Gly Lys Ser Ser Gly Val Pro
210                 215                 220

Pro Glu Val Phe Thr Arg Val Ser Ser Phe Leu Pro Trp Ile Arg Thr
225                 230                 235                 240

Thr Met Arg Ser Phe Lys Leu Leu Asp Gln Met Glu Thr Pro Leu
                245                 250                 255
```

<210> SEQ ID NO 6
<211> LENGTH: 924
<212> TYPE: DNA
<213> ORGANISM: Homo sapiens

<400> SEQUENCE: 6

```
gcacagcagc aactgactgg gcagcctttc aggaaagatg cagccactcc tgcttctgct      60
ggcctttctc ctacccactg gggctgaggc aggggagatc atcggaggcc gggagagcag     120
gccccactcc cgcccctaca tggcgtatct tcagatccag agtccagcag gtcagagcag     180
atgtggaggg ttcctggtgc gagaagactt tgtgctgaca gcagctcatt gctggggaag     240
```

-continued

```
caatataaat gtcaccctgg gcgcccacaa tatccagaga cgggaaaaca cccagcaaca    300
catcactgcg cgcagagcca tccgccaccc tcaatataat cagcggacca tccagaatga    360
catcatgtta ttgcagctga gcagaagagt cagacggaat cgaaacgtga acccagtggc    420
tctgcctaga gcccaggagg gactgagacc cgggacgctg tgcactgtgg ccggctgggg    480
cagggtcagc atgaggaggg gaacagatac actccgagag gtgcagctga gagtgcagag    540
ggataggcag tgcctccgca tcttcggttc ctacgacccc cgaaggcaga tttgtgtggg    600
ggaccggcgg gaacggaagg ctgccttcaa gggggattcc ggaggccccc tgctgtgtaa    660
caatgtggcc cacggcatcg tctcctatgg aaagtcgtca ggggttcctc cagaagtctt    720
caccagggtc tcaagtttcc tgccctggat aaggacaaca atgagaagct caaactgct     780 ggatcagatg agaccccccc tgtgactgac tcttcttctc ggggacacag gccagctcca    840
cagtgttgcc agagccttaa taaacgtcca cagagtataa ataaccaatt cctcatttgt    900
tcattaaacg tcattcagta ctta                                           924
```

<210> SEQ ID NO 7
<211> LENGTH: 750
<212> TYPE: PRT
<213> ORGANISM: Homo sapiens

<400> SEQUENCE: 7

```
Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Ala Ala Asn
         35                  40                  45

Asp Val Ser Phe Ala Thr Ile Arg Phe His Asp Leu Leu Ser Gln Leu
     50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
```

-continued

```
                245                 250                 255
Asp Gln Leu Gln Asn Trp Phe Thr Ile Val Ala Glu Ser Leu Gln Gln
            260                 265                 270
Val Arg Gln Gln Leu Lys Lys Leu Glu Glu Leu Glu Gln Lys Tyr Thr
        275                 280                 285
Tyr Glu His Asp Pro Ile Thr Lys Asn Lys Gln Val Leu Trp Asp Arg
    290                 295                 300
Thr Phe Ser Leu Phe Gln Gln Leu Ile Gln Ser Ser Phe Val Val Glu
305                 310                 315                 320
Arg Gln Pro Cys Met Pro Thr His Pro Gln Arg Pro Leu Val Leu Lys
                325                 330                 335
Thr Gly Val Gln Phe Thr Val Lys Leu Arg Leu Leu Val Lys Leu Gln
            340                 345                 350
Glu Leu Asn Tyr Asn Leu Lys Val Lys Val Leu Phe Asp Lys Asp Val
        355                 360                 365
Asn Glu Arg Asn Thr Val Lys Gly Phe Arg Lys Phe Asn Ile Leu Gly
    370                 375                 380
Thr His Thr Lys Val Met Asn Met Glu Glu Ser Thr Asn Gly Ser Leu
385                 390                 395                 400
Ala Ala Glu Phe Arg His Leu Gln Leu Lys Glu Gln Lys Asn Ala Gly
                405                 410                 415
Thr Arg Thr Asn Glu Gly Pro Leu Ile Val Thr Glu Glu Leu His Ser
            420                 425                 430
Leu Ser Phe Glu Thr Gln Leu Cys Gln Pro Gly Leu Val Ile Asp Leu
        435                 440                 445
Glu Thr Thr Ser Leu Pro Val Val Val Ile Ser Asn Val Ser Gln Leu
    450                 455                 460
Pro Ser Gly Trp Ala Ser Ile Leu Trp Tyr Asn Met Leu Val Ala Glu
465                 470                 475                 480
Pro Arg Asn Leu Ser Phe Phe Leu Thr Pro Pro Cys Ala Arg Trp Ala
                485                 490                 495
Gln Leu Ser Glu Val Leu Ser Trp Gln Phe Ser Ser Val Thr Lys Arg
            500                 505                 510
Gly Leu Asn Val Asp Gln Leu Asn Met Leu Gly Glu Lys Leu Leu Gly
        515                 520                 525
Pro Asn Ala Ser Pro Asp Gly Leu Ile Pro Trp Thr Arg Phe Cys Lys
    530                 535                 540
Glu Asn Ile Asn Asp Lys Asn Phe Pro Phe Trp Leu Trp Ile Glu Ser
545                 550                 555                 560
Ile Leu Glu Leu Ile Lys Lys His Leu Leu Pro Leu Trp Asn Asp Gly
                565                 570                 575
Cys Ile Met Gly Phe Ile Ser Lys Glu Arg Glu Arg Ala Leu Leu Lys
            580                 585                 590
Asp Gln Gln Pro Gly Thr Phe Leu Leu Arg Phe Ser Glu Ser Ser Arg
        595                 600                 605
Glu Gly Ala Ile Thr Phe Thr Trp Val Glu Arg Ser Gln Asn Gly Gly
    610                 615                 620
Glu Pro Asp Phe His Ala Val Glu Pro Tyr Thr Lys Lys Glu Leu Ser
625                 630                 635                 640
Ala Val Thr Phe Pro Asp Ile Ile Arg Asn Tyr Lys Val Met Ala Ala
                645                 650                 655
Glu Asn Ile Pro Glu Asn Pro Leu Lys Tyr Leu Tyr Pro Asn Ile Asp
            660                 665                 670
```

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
        690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750

<210> SEQ ID NO 8
<211> LENGTH: 4326
<212> TYPE: DNA
<213> ORGANISM: Homo sapiens

<400> SEQUENCE: 8
gctgagcgcg gagccgcccg gtgattggtg ggggcggaag ggggccgggc gccagcgctg       60 cctttctcc tgccgggtag tttcgctttc ctgcgcagag tctgcggagg ggctcggctg      120
caccgggggg atcgcgcctg cagaccccca gaccgagcag aggcgaccca gcgcgctcgg      180
gagaggctgc accgccgcgc ccccgcctag cccttccgga tcctgcgcgc agaaaagttt      240
catttgctgt atgccatcct cgagagctgt ctaggttaac gttcgcactc tgtgtatata      300
acctcgacag tcttggcacc taacgtgctg tgcgtagctg ctcctttggt tgaatcccca      360
ggcccttgtt ggggcacaag gtggcaggat gtctcagtgg tacgaacttc agcagcttga      420
ctcaaaattc ctggagcagg ttcaccagct ttatgatgac agttttccca tggaaatcag      480
acagtacctg gcacagtggt tagaaaagca agactgggag cacgctgcca atgatgtttc      540
atttgccacc atccgttttc atgacctcct gtcacagctg atgatcaat atagtcgctt       600 ttctttggag aataacttct tgctacagca ataacataagg aaaagcaagc gtaatcttca     660
ggataatttt caggaagacc aatccagat gtctatgatc atttacagct gtctgaagga      720
agaaaggaaa attctggaaa acgcccagag atttaatcag gctcagtcgg ggaatattca      780
gagcacagtg atgttagaca aacagaaaga gcttgacagt aaagtcagaa atgtgaagga      840
caaggttatg tgtatagagc atgaaatcaa gagcctggaa gatttacaag atgaatatga      900
cttcaaatgc aaaaccttgc agaacagaga cacgagacc aatggtgtgg caaagagtga       960
tcagaaacaa gaacagctgt tactcaagaa gatgtattta atgcttgaca ataagagaaa     1020
ggaagtagtt cacaaaataa tagagttgct gaatgtcact gaacttaccc agaatgccct     1080
gattaatgat gaactagtgg agtggaagcg gagacagcag agcgcctgta ttgggggggcc    1140 gcccaatgct tgcttggatc agctgcagaa ctggttcact atagttgcgg agagtctgca     1200
gcaagttcgg cagcagctta aaagttgga ggaattggaa cagaaataca cctacgaaca     1260
tgaccctatc acaaaaaaca aacaagtgtt atgggaccgc accttcagtc ttttccagca    1320
gctcattcag agctcgtttg tggtggaaag acagccctgc atgccaacgc accctcagag    1380
gccgctggtc ttgaagacag gggtccagtt cactgtgaag ttgagactgt tggtgaaatt    1440
gcaagagctg aattataatt tgaaagtcaa agtcttattt gataaagatg tgaatgagag    1500
aaatacagta aaaggattta ggaagttcaa cattttgggc acgcacacaa agtgatgaa      1560 catggaggag tccaccaatg gcagtctggc ggctgaattt cggcacctgc aattgaaaga    1620
acagaaaaat gctggcacca gaacgaatga gggtcctctc atcgttactg aagagcttca    1680

```
ctcccttagt tttgaaaccc aattgtgcca gcctggtttg gtaattgacc tcgagacgac    1740
ctctctgccc gttgtggtga tctccaacgt cagccagctc ccgagcggtt gggcctccat    1800
cctttggtac aacatgctgg tggcggaacc caggaatctg tccttcttcc tgactccacc    1860
atgtgcacga tgggctcagc tttcagaagt gctgagttgg cagttttctt ctgtcaccaa    1920
aagaggtctc aatgtggacc agctgaacat gttgggagag aagcttcttg gtcctaacgc    1980
cagccccgat ggtctcattc cgtggacgag gttttgtaag gaaatataaa atgataaaaa    2040
ttttcccttc tggctttgga ttgaaagcat cctagaactc attaaaaaac acctgctccc    2100
tctctggaat gatgggtgca tcatgggctt catcagcaag gagcgagagc gtgccctgtt    2160
gaaggaccag cagccgggga ccttcctgct gcggttcagt gagagctccc gggaaggggc    2220
catcacattc acatgggtgg agcggtccca aacggaggc gaacctgact tccatgcggt    2280
tgaaccctac acgaagaaag aactttctgc tgttactttc cctgacatca ttcgcaatta    2340
caaagtcatg gctgctgaga atattcctga gaatcccctg aagtatctgt atccaaatat    2400
tgacaaagac catgcctttg gaaagtatta ctccaggcca aaggaagcac cagagccaat    2460
ggaacttgat ggccctaaag gaactggata tatcaagact gagttgattt ctgtgtctga    2520
agttcacccT tctagacttc agaccacaga caacctgctc cccatgtctc ctgaggagtt    2580
tgacgaggtg tctcggatag tgggctctgt agaattcgac agtatgatga acacagtata    2640
gagcatgaat ttttttcatc ttctctggcg acagttttcc ttctcatctg tgattccctc    2700
ctgctactct gttccttcac atcctgtgtt tctagggaaa tgaaagaaag gccagcaaat    2760
tcgctgcaac ctgttgatag caagtgaatt tttctctaac tcagaaacat cagttactct    2820
gaagggcatc atgcatctta ctgaaggtaa aattgaaagg cattctctga agagtggggtt    2880
tcacaagtga aaaacatcca gatacaccca agtatcagg acgagaatga gggtcctttg    2940
ggaaaggaga agttaagcaa catctagcaa atgttatgca taagtcagt gcccaactgt    3000
tataggttgt tggataaatc agtggttatt tagggaactg cttgacgtag gaacggtaaa    3060
tttctgtggg agaattctta catgtttctc ttgctttaag tgtaactggc agttttccat    3120
tggtttacct gtgaaatagt tcaaagccaa gtttatatac aattatatca gtcctctttc    3180
aaaggtagcc atcatggatc tggtaggggg aaaatgtgta ttttattaca tctttcacat    3240
tggctatta agacaaaga caaattctgt ttccttgagaa gagaatatta gctttactgt    3300
ttgttatggc ttaatgacac tagctaatat caatagaagg atgtacattt ccaaattcac    3360
aagttgtgtt tgatatccaa agctgaatac attctgcttt catcttggtc acatacaatt    3420
atttttacag ttctcccaag ggagttaggc tattcacaac cactcattca aaagttgaaa    3480
ttaaccatag atgtagataa actcagaaat ttaattcatg tttcttaaat gggctacttt    3540
gtcctttttg ttattagggt ggtatttagt ctattagcca caaaattggg aaaggagtag    3600
aaaaagcagt aactgacaac ttgaataata caccagagat aatatgagaa tcagatcatt    3660
tcaaaactca tttcctatgt aactgcattg agaactgcat atgtttcgct gatatatgtg    3720
ttttcacat ttgcgaatgg ttccattctc tctcctgtac ttttttccaga cactttttg    3780
agtggatgat gtttcgtgaa gtatactgta ttttaccttt ttccttcct tatcactgac    3840
acaaaaagta gattaagaga tgggtttgac aaggttcttc ccttttacat actgctgtct    3900
atgtggctgt atcttgtttt tccactactg ctaccacaac tatattatca tgcaaatgct    3960
gtattcttct ttggtggaga taaagatttc ttgagttttg ttttaaaatt aaagctaaag    4020
```

```
tatctgtatt gcattaaata taatatgcac acagtgcttt ccgtggcact gcatacaatc    4080
tgaggcctcc tctctcagtt tttatataga tggcgagaac ctaagtttca gttgatttta    4140
caattgaaat gactaaaaaa caaagaagac aacattaaaa caatattgtt tctaattgct    4200
gaggtttagc tgtcagttct ttttgcccctt tgggaattcg gcatggtttc attttactgc    4260
actagccaag agactttact tttaagaagt attaaaattc taaaattcaa aaaaaaaaaa    4320
aaaaaa                                                               4326
```

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Pro Phe
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-(Methoxysuccinyl)-Ala
<220> FEATURE:
<221> NAME/KEY: MOD_RES
<222> LOCATION: (4)
<223> OTHER INFORMATION: Phe-chloromethyl ketone

<400> SEQUENCE: 10

Ala Ala Pro Phe
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Pro Val
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-(Methoxysuccinyl)-Ala
<220> FEATURE:
<221> NAME/KEY: MOD_RES
<222> LOCATION: (4)
<223> OTHER INFORMATION: Val-chloromethyl ketone

```
<400> SEQUENCE: 12

Ala Ala Pro Val
  1

<210> SEQ ID NO 13
<211> LENGTH: 70
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Acetyl-Thr
<220> FEATURE:
<221> NAME/KEY: MOD_RES
<222> LOCATION: (70)
<223> OTHER INFORMATION: Gly-OH

<400> SEQUENCE: 13

Thr Glu Phe Gly Ser Glu Leu Lys Ser Phe Pro Glu Val Val Gly Lys
  1               5                  10                  15

Thr Val Asp Gln Ala Arg Glu Tyr Phe Thr Leu His Tyr Pro Gln Tyr
             20                  25                  30

Asp Val Tyr Phe Leu Pro Glu Gly Ser Pro Val Thr Leu Asp Leu Arg
         35                  40                  45

Tyr Asn Arg Val Arg Val Phe Tyr Asn Pro Gly Thr Asn Val Val Asn
     50                  55                  60

His Val Pro His Val Gly
 65                  70

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Val Thr Leu
  1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Pro Val Thr Leu Asp Leu Arg Tyr
  1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Thr Glu Ala Ala Ala Ala Thr Ala Gly Ile Ala Thr Phe Cys
```

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Leu Met Phe Glu Glu Asn Phe Thr Ala Asp His Pro Phe
 1               5                  10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Thr Glu Ala Ala Ala Ala Thr Gly Gly Ile Ala Thr Phe Cys
 1               5                  10                  15

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Leu Leu Pro Glu Glu Glu Phe Thr Val Asp His Pro Phe
 1               5                  10

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Thr Glu Ala Ala Ala Ala Thr Gly Gly Ile Ile Gln Val Leu Cys
 1               5                  10                  15

Glu Lys Met Pro Thr Pro Gln Glu Val Phe Thr Val Asp His Pro Phe
                20                  25                  30

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ala-chloromethyl ketone

<400> SEQUENCE: 21

Ala Ala Pro Ala
 1